US008418085B2

(12) United States Patent
Snook et al.

(10) Patent No.: US 8,418,085 B2
(45) Date of Patent: Apr. 9, 2013

(54) GESTURE COACH

(75) Inventors: Gregory N. Snook, Sammamish, WA (US); Stephen Latta, Seattle, WA (US); Kevin Geisner, Seattle, WA (US); Darren Alexander Bennett, Seattle, WA (US); Kudo Tsunoda, Seattle, WA (US); Alex Kipman, Redmond, WA (US); Kathryn Stone Perez, Shoreline, WA (US)

(73) Assignee: Microsoft Corporation, Redmond, WA (US)

( * ) Notice: Subject to any disclaimer, the term of this patent is extended or adjusted under 35 U.S.C. 154(b) by 442 days.

(21) Appl. No.: 12/474,453

(22) Filed: May 29, 2009

(65) Prior Publication Data
US 2010/0306712 A1 Dec. 2, 2010

(51) Int. Cl.
G06F 3/00 (2006.01)
G06F 3/033 (2006.01)

(52) U.S. Cl.
USPC .............................. 715/863; 715/707; 715/709

(58) Field of Classification Search .................. 715/709, 715/714, 863, 707
See application file for complete search history.

(56) References Cited

U.S. PATENT DOCUMENTS

| | | | |
|---|---|---|---|
| 4,627,620 A | 12/1986 | Yang | |
| 4,630,910 A | 12/1986 | Ross et al. | |
| 4,645,458 A | 2/1987 | Williams | |
| 4,695,953 A | 9/1987 | Blair et al. | |
| 4,702,475 A | 10/1987 | Elstein et al. | |
| 4,711,543 A | 12/1987 | Blair et al. | |
| 4,751,642 A | 6/1988 | Silva et al. | |
| 4,796,997 A | 1/1989 | Svetkoff et al. | |
| 4,809,065 A | 2/1989 | Harris et al. | |
| 4,817,950 A | 4/1989 | Goo | |
| 4,843,568 A | 6/1989 | Krueger et al. | |
| 4,893,183 A | 1/1990 | Nayar | |
| 4,901,362 A | 2/1990 | Terzian | |
| 4,925,189 A | 5/1990 | Braeunig | |

(Continued)

FOREIGN PATENT DOCUMENTS

| | | |
|---|---|---|
| AU | 19259/92 | 2/1995 |
| CN | 101202994 A | 6/2008 |
| CN | 201254344 B | 6/2010 |

(Continued)

OTHER PUBLICATIONS

"Signal Processing Institute," http://ltswww.epfl.ch/~alahi/student₁₃ projects/proposals.shtml#4, downloaded Feb. 2, 2009, pp. 1-4.

(Continued)

*Primary Examiner* — Weilun Lo
*Assistant Examiner* — Truc Chuong
(74) *Attorney, Agent, or Firm* — Woodcock Washburn LLP

(57) ABSTRACT

A capture device may capture a user's motion and a display device may display a model that maps to the user's motion, including gestures that are applicable for control. A user may be unfamiliar with a system that maps the user's motions or not know what gestures are applicable for an executing application. A user may not understand or know how to perform gestures that are applicable for the executing application. User motion data and/or outputs of filters corresponding to gestures may be analyzed to determine those cases where assistance to the user on performing the gesture is appropriate.

19 Claims, 17 Drawing Sheets

U.S. PATENT DOCUMENTS

| | | | |
|---|---|---|---|
| 5,101,444 A | 3/1992 | Wilson et al. |
| 5,148,154 A | 9/1992 | MacKay et al. |
| 5,184,295 A | 2/1993 | Mann |
| 5,229,754 A | 7/1993 | Aoki et al. |
| 5,229,756 A | 7/1993 | Kosugi et al. |
| 5,239,463 A | 8/1993 | Blair et al. |
| 5,239,464 A | 8/1993 | Blair et al. |
| 5,288,078 A | 2/1994 | Capper et al. |
| 5,295,491 A | 3/1994 | Gevins |
| 5,320,538 A | 6/1994 | Baum |
| 5,347,306 A | 9/1994 | Nitta |
| 5,385,519 A | 1/1995 | Hsu et al. |
| 5,405,152 A | 4/1995 | Katanics et al. |
| 5,417,210 A | 5/1995 | Funda et al. |
| 5,423,554 A | 6/1995 | Davis |
| 5,454,043 A | 9/1995 | Freeman |
| 5,469,740 A | 11/1995 | French et al. |
| 5,486,001 A | 1/1996 | Baker |
| 5,495,576 A | 2/1996 | Ritchey |
| 5,516,105 A | 5/1996 | Eisenbrey et al. |
| 5,524,637 A | 6/1996 | Erickson |
| 5,534,917 A | 7/1996 | MacDougall |
| 5,563,988 A | 10/1996 | Maes et al. |
| 5,577,981 A | 11/1996 | Jarvik |
| 5,580,249 A | 12/1996 | Jacobsen et al. |
| 5,594,469 A | 1/1997 | Freeman et al. |
| 5,597,309 A | 1/1997 | Riess |
| 5,616,078 A | 4/1997 | Oh |
| 5,617,312 A | 4/1997 | Iura et al. |
| 5,638,300 A | 6/1997 | Johnson |
| 5,641,288 A | 6/1997 | Zaenglein |
| 5,682,196 A | 10/1997 | Freeman |
| 5,682,229 A | 10/1997 | Wangler |
| 5,690,582 A | 11/1997 | Ulrich et al. |
| 5,703,367 A | 12/1997 | Hashimoto et al. |
| 5,704,837 A | 1/1998 | Iwasaki et al. |
| 5,715,834 A | 2/1998 | Bergamasco et al. |
| 5,875,108 A | 2/1999 | Hoffberg et al. |
| 5,877,803 A | 3/1999 | Wee et al. |
| 5,904,484 A * | 5/1999 | Burns ........................... 434/252 |
| 5,913,727 A | 6/1999 | Ahdoot |
| 5,933,125 A | 8/1999 | Fernie |
| 5,980,256 A | 11/1999 | Carmein |
| 5,989,157 A | 11/1999 | Walton |
| 5,995,649 A | 11/1999 | Marugame |
| 6,005,548 A | 12/1999 | Latypov et al. |
| 6,009,210 A | 12/1999 | Kang |
| 6,054,991 A | 4/2000 | Crane et al. |
| 6,057,909 A | 5/2000 | Yahav et al. |
| 6,066,075 A | 5/2000 | Poulton |
| 6,072,494 A | 6/2000 | Nguyen |
| 6,073,489 A | 6/2000 | French et al. |
| 6,075,895 A | 6/2000 | Qiao et al. |
| 6,077,201 A | 6/2000 | Cheng et al. |
| 6,098,458 A | 8/2000 | French et al. |
| 6,100,517 A | 8/2000 | Yahav et al. |
| 6,100,896 A | 8/2000 | Strohecker et al. |
| 6,101,289 A | 8/2000 | Kellner |
| 6,128,003 A | 10/2000 | Smith et al. |
| 6,130,677 A | 10/2000 | Kunz |
| 6,141,463 A | 10/2000 | Covell et al. |
| 6,147,678 A | 11/2000 | Kumar et al. |
| 6,152,856 A | 11/2000 | Studor et al. |
| 6,159,100 A | 12/2000 | Smith |
| 6,173,066 B1 | 1/2001 | Peurach et al. |
| 6,181,343 B1 | 1/2001 | Lyons |
| 6,188,777 B1 | 2/2001 | Darrell et al. |
| 6,215,890 B1 | 4/2001 | Matsuo et al. |
| 6,215,898 B1 | 4/2001 | Woodfill et al. |
| 6,226,396 B1 | 5/2001 | Marugame |
| 6,229,913 B1 | 5/2001 | Nayar et al. |
| 6,256,033 B1 | 7/2001 | Nguyen |
| 6,256,400 B1 | 7/2001 | Takata et al. |
| 6,283,860 B1 | 9/2001 | Lyons et al. |
| 6,289,112 B1 | 9/2001 | Jain et al. |
| 6,299,308 B1 | 10/2001 | Voronka et al. |
| 6,308,565 B1 | 10/2001 | French et al. |
| 6,316,934 B1 | 11/2001 | Amorai-Moriya et al. |
| 6,363,160 B1 | 3/2002 | Bradski et al. |
| 6,384,819 B1 | 5/2002 | Hunter |
| 6,411,744 B1 | 6/2002 | Edwards |
| 6,430,997 B1 | 8/2002 | French et al. |
| 6,476,834 B1 | 11/2002 | Doval et al. |
| 6,496,598 B1 | 12/2002 | Harman |
| 6,498,628 B2 | 12/2002 | Iwamura |
| 6,502,515 B2 | 1/2003 | Burckhardt et al. |
| 6,503,195 B1 | 1/2003 | Keller et al. |
| 6,512,838 B1 | 1/2003 | Rafii et al. |
| 6,514,081 B1 * | 2/2003 | Mengoli ....................... 434/252 |
| 6,539,931 B2 | 4/2003 | Trajkovic et al. |
| 6,570,555 B1 | 5/2003 | Prevost et al. |
| 6,633,294 B1 | 10/2003 | Rosenthal et al. |
| 6,640,202 B1 | 10/2003 | Dietz et al. |
| 6,661,918 B1 | 12/2003 | Gordon et al. |
| 6,674,877 B1 | 1/2004 | Jojic et al. |
| 6,681,031 B2 | 1/2004 | Cohen et al. |
| 6,714,665 B1 | 3/2004 | Hanna et al. |
| 6,731,799 B1 | 5/2004 | Sun et al. |
| 6,738,066 B1 | 5/2004 | Nguyen |
| 6,765,726 B2 | 7/2004 | French et al. |
| 6,771,277 B2 | 8/2004 | Ohba |
| 6,788,809 B1 | 9/2004 | Grzeszczuk et al. |
| 6,801,637 B2 | 10/2004 | Voronka et al. |
| 6,873,723 B1 | 3/2005 | Aucsmith et al. |
| 6,876,496 B2 | 4/2005 | French et al. |
| 6,937,742 B2 | 8/2005 | Roberts et al. |
| 6,950,534 B2 | 9/2005 | Cohen et al. |
| 7,003,134 B1 | 2/2006 | Covell et al. |
| 7,006,236 B2 | 2/2006 | Tomasi et al. |
| 7,036,094 B1 | 4/2006 | Cohen et al. |
| 7,038,855 B2 | 5/2006 | French et al. |
| 7,039,676 B1 | 5/2006 | Day et al. |
| 7,042,440 B2 | 5/2006 | Pryor et al. |
| 7,050,177 B2 | 5/2006 | Tomasi et al. |
| 7,050,606 B2 | 5/2006 | Paul et al. |
| 7,058,204 B2 | 6/2006 | Hildreth et al. |
| 7,060,957 B2 | 6/2006 | Lange et al. |
| 7,113,918 B1 | 9/2006 | Ahmad et al. |
| 7,121,946 B2 | 10/2006 | Paul et al. |
| 7,151,530 B2 | 12/2006 | Roeber et al. |
| 7,170,492 B2 | 1/2007 | Bell |
| 7,184,048 B2 | 2/2007 | Hunter |
| 7,202,898 B1 | 4/2007 | Braun et al. |
| 7,222,078 B2 | 5/2007 | Abelow |
| 7,224,384 B1 | 5/2007 | Iddan et al. |
| 7,227,526 B2 | 6/2007 | Hildreth et al. |
| 7,259,747 B2 | 8/2007 | Bell |
| 7,293,356 B2 | 11/2007 | Sohn et al. |
| 7,308,112 B2 | 12/2007 | Fujimura et al. |
| 7,310,431 B2 | 12/2007 | Gokturk et al. |
| 7,317,836 B2 | 1/2008 | Fujimura et al. |
| 7,340,077 B2 | 3/2008 | Gokturk et al. |
| 7,348,963 B2 | 3/2008 | Bell |
| 7,359,121 B2 | 4/2008 | French et al. |
| 7,367,887 B2 | 5/2008 | Watabe et al. |
| 7,379,563 B2 | 5/2008 | Shamaie |
| 7,379,566 B2 | 5/2008 | Hildreth |
| 7,389,591 B2 | 6/2008 | Jaiswal et al. |
| 7,412,077 B2 | 8/2008 | Li et al. |
| 7,421,093 B2 | 9/2008 | Hildreth et al. |
| 7,430,312 B2 | 9/2008 | Gu |
| 7,436,496 B2 | 10/2008 | Kawahito |
| 7,450,736 B2 | 11/2008 | Yang et al. |
| 7,452,275 B2 | 11/2008 | Kuraishi |
| 7,460,690 B2 | 12/2008 | Cohen et al. |
| 7,489,812 B2 | 2/2009 | Fox et al. |
| 7,536,032 B2 | 5/2009 | Bell |
| 7,555,142 B2 | 6/2009 | Hildreth et al. |
| 7,560,701 B2 | 7/2009 | Oggier et al. |
| 7,570,805 B2 | 8/2009 | Gu |
| 7,574,020 B2 | 8/2009 | Shamaie |
| 7,576,727 B2 | 8/2009 | Bell |
| 7,590,262 B2 | 9/2009 | Fujimura et al. |
| 7,593,552 B2 | 9/2009 | Higaki et al. |
| 7,598,942 B2 | 10/2009 | Underkoffler et al. |
| 7,607,509 B2 | 10/2009 | Schmiz et al. |
| 7,620,202 B2 | 11/2009 | Fujimura et al. |

| | | |
|---|---|---|
| 7,668,340 B2 | 2/2010 | Cohen et al. |
| 7,680,298 B2 | 3/2010 | Roberts et al. |
| 7,683,954 B2 | 3/2010 | Ichikawa et al. |
| 7,684,592 B2 | 3/2010 | Paul et al. |
| 7,701,439 B2 | 4/2010 | Hillis et al. |
| 7,702,130 B2 | 4/2010 | Im et al. |
| 7,704,135 B2 | 4/2010 | Harrison, Jr. |
| 7,710,391 B2 | 5/2010 | Bell et al. |
| 7,729,530 B2 | 6/2010 | Antonov et al. |
| 7,746,345 B2 | 6/2010 | Hunter |
| 7,760,182 B2 | 7/2010 | Ahmad et al. |
| 7,809,167 B2 | 10/2010 | Bell |
| 7,834,846 B1 | 11/2010 | Bell |
| 7,852,262 B2 | 12/2010 | Namineni et al. |
| RE42,256 E | 3/2011 | Edwards |
| 7,898,522 B2 | 3/2011 | Hildreth et al. |
| 8,035,612 B2 | 10/2011 | Bell et al. |
| 8,035,614 B2 | 10/2011 | Bell et al. |
| 8,035,624 B2 | 10/2011 | Bell et al. |
| 8,072,470 B2 | 12/2011 | Marks |
| 2004/0155962 A1 | 8/2004 | Marks |
| 2004/0193413 A1* | 9/2004 | Wilson et al. ............ 704/243 |
| 2004/0207597 A1 | 10/2004 | Marks |
| 2005/0059488 A1 | 3/2005 | Larsen et al. |
| 2005/0215319 A1 | 9/2005 | Rigopulos et al. |
| 2006/0188144 A1 | 8/2006 | Sasaki et al. |
| 2006/0210958 A1 | 9/2006 | Rimas-Ribikauskas et al. |
| 2006/0239558 A1 | 10/2006 | Rafii et al. |
| 2007/0013718 A1 | 1/2007 | Ohba |
| 2007/0060336 A1 | 3/2007 | Marks et al. |
| 2007/0098222 A1 | 5/2007 | Porter et al. |
| 2007/0216894 A1 | 9/2007 | Garcia et al. |
| 2007/0260984 A1 | 11/2007 | Marks et al. |
| 2007/0279485 A1 | 12/2007 | Ohba et al. |
| 2007/0283296 A1 | 12/2007 | Nilsson |
| 2007/0298882 A1 | 12/2007 | Marks et al. |
| 2008/0001951 A1 | 1/2008 | Marks et al. |
| 2008/0026838 A1 | 1/2008 | Dunstan et al. |
| 2008/0059578 A1* | 3/2008 | Albertson et al. ........ 709/204 |
| 2008/0062257 A1 | 3/2008 | Corson |
| 2008/0100620 A1 | 5/2008 | Nagai et al. |
| 2008/0124690 A1 | 5/2008 | Redlich |
| 2008/0126937 A1 | 5/2008 | Pachet |
| 2008/0134102 A1 | 6/2008 | Movold et al. |
| 2008/0152191 A1 | 6/2008 | Fujimura et al. |
| 2008/0163130 A1* | 7/2008 | Westerman ............ 715/863 |
| 2008/0178126 A1 | 7/2008 | Beeck |
| 2008/0215972 A1 | 9/2008 | Zalewski et al. |
| 2008/0215973 A1 | 9/2008 | Zalewski et al. |
| 2008/0234023 A1* | 9/2008 | Mullahkhel et al. ........... 463/7 |
| 2009/0085864 A1 | 4/2009 | Kutliroff et al. |
| 2009/0141933 A1 | 6/2009 | Wagg |
| 2009/0167679 A1 | 7/2009 | Klier et al. |
| 2009/0221368 A1 | 9/2009 | Yen et al. |
| 2010/0093435 A1 | 4/2010 | Glaser et al. |
| 2010/0295783 A1* | 11/2010 | El Dokor et al. ......... 345/158 |

FOREIGN PATENT DOCUMENTS

| | | |
|---|---|---|
| EP | 0583061 A2 | 2/1994 |
| JP | 08044490 A1 | 2/1996 |
| WO | WO92/21412 | 12/1992 |
| WO | 93/10708 A1 | 6/1993 |
| WO | 97/17598 A1 | 5/1997 |
| WO | WO 99/15863 A1 | 4/1999 |
| WO | 99/44698 A1 | 9/1999 |
| WO | WO 01/59975 A3 | 1/2002 |
| WO | WO 02/082249 A2 | 10/2002 |
| WO | WO03015056 A2 | 2/2003 |
| WO | WO 03/001722 A3 | 3/2003 |
| WO | WO 03/046706 A1 | 6/2003 |
| WO | WO 03/073359 A3 | 11/2003 |
| WO | WO 03/054683 A3 | 12/2003 |
| WO | WO 03/071410 A3 | 3/2004 |
| WO | WO 2009/059065 A1 | 5/2009 |

OTHER PUBLICATIONS

Kwon et al., "Combining Body Sensors and Visual Sensors for Motion Training," Computer Graphics Laboratory, http://graphics.ethz.ch/~dkwon/downloads/publications/ace05/kwo05_ace.pdf, downloaded 2009, pp. 1-8.

Raymer, A., "Gestures and Words: Facilitating Recovery in Aphasia," The ASHA Leader, Jun. 19, 2007, 12(8), http://www.asha.org/about/publications/leader-online/archives/2007/070619/f070619a.htm, pp. 8-11, (printout) pp. 1-3.

PCT Application No. PCT/US2010/036005: International Search Report and Written Opinion of the International Searching Authority, Dec. 24, 2010, 8 pages.

Qian et al., "A Gesture-Driven Multimodal Interactive Dance System", IEEE International Conference on Multimedia and Expo, Taipei, Jun. 2004, 3, 1579-1582.

Shivappa et al., "Person Tracking with Audio-Visual Cues Using Iterative Decoding Framework", IEEE Fifth International Conference on Advanced Video and Signal Based Surveillance, AVSS '08, Santa Fe, NM, Sep. 1-3, 2008, 260-267.

Kanade et al., "A Stereo Machine for Video-rate Dense Depth Mapping and Its New Applications", IEEE Computer Society Conference on Computer Vision and Pattern Recognition, 1996, pp. 196-202,The Robotics Institute, Carnegie Mellon University, Pittsburgh, PA.

Miyagawa et al., "CCD-Based Range Finding Sensor", Oct. 1997, pp. 1648-1652, vol. 44 No. 10, IEEE Transactions on Electron Devices.

Rosenhahn et al., "Automatic Human Model Generation", 2005, pp. 41-48, University of Auckland (CITR), New Zealand.

Aggarwal et al., "Human Motion Analysis: A Review", IEEE Nonrigid and Articulated Motion Workshop, 1997, University of Texas at Austin, Austin, TX.

Shao et al., "An Open System Architecture for a Multimedia and Multimodal User Interface", Aug. 24, 1998, Japanese Society for Rehabilitation of Persons with Disabilities (JSRPD), Japan.

Kohler, "Special Topics of Gesture Recognition Applied in Intelligent Home Environments", In Proceedings of the Gesture Workshop, 1998, pp. 285-296, Germany.

Kohler, "Vision Based Remote Control in Intelligent Home Environments", University of Erlangen-Nuremberg/Germany, 1996, pp. 147-154, Germany.

Kohler, "Technical Details and Ergonomical Aspects of Gesture Recognition applied in Intelligent Home Environments", 1997, Germany.

Hasegawa et al., "Human-Scale Haptic Interaction with a Reactive Virtual Human in a Real-Time Physics Simulator", Jul. 2006, vol. 4, No. 3, Article 6C, ACM Computers in Entertainment, New York, NY.

Qian et al., "A Gesture-Driven Multimodal Interactive Dance System", Jun. 2004, pp. 1579-1582, IEEE International Conference on Multimedia and Expo (ICME), Taipei, Taiwan.

Zhao, "Dressed Human Modeling, Detection, and Parts Localization", 2001, The Robotics Institute, Carnegie Mellon University, Pittsburgh, PA.

He, "Generation of Human Body Models", Apr. 2005, University of Auckland, New Zealand.

Isard et al., "CONDENSATION—Conditional Density Propagation for Visual Tracking", 1998, pp. 5-28, International Journal of Computer Vision 29(1), Netherlands.

Livingston, "Vision-based Tracking with Dynamic Structured Light for Video See-through Augmented Reality", 1998, University of North Carolina at Chapel Hill, North Carolina, USA.

Wren et al., "Pfinder: Real-Time Tracking of the Human Body", MIT Media Laboratory Perceptual Computing Section Technical Report No. 353, Jul. 1997, vol. 19, No. 7, pp. 780-785, IEEE Transactions on Pattern Analysis and Machine Intelligence, Caimbridge, MA.

Breen et al., "Interactive Occlusion and Collusion of Real and Virtual Objects in Augmented Reality", Technical Report ECRC-95-02, 1995, European Computer-Industry Research Center GmbH, Munich, Germany.

Freeman et al., "Television Control by Hand Gestures", Dec. 1994, Mitsubishi Electric Research Laboratories, TR94-24, Caimbridge, MA.

Hongo et al., "Focus of Attention for Face and Hand Gesture Recognition Using Multiple Cameras", Mar. 2000, pp. 156-161, 4th IEEE International Conference on Automatic Face and Gesture Recognition, Grenoble, France.

Pavlovic et al., "Visual Interpretation of Hand Gestures for Human-Computer Interaction: A Review", Jul. 1997, pp. 677-695, vol. 19, No. 7, IEEE Transactions on Pattern Analysis and Machine Intelligence.

Azarbayejani et al., "Visually Controlled Graphics", Jun. 1993, vol. 15, No. 6, IEEE Transactions on Pattern Analysis and Machine Intelligence.

Granieri et al., "Simulating Humans in VR", The British Computer Society, Oct. 1994, Academic Press.

Brogan et al., "Dynamically Simulated Characters in Virtual Environments", Sep./Oct. 1998, pp. 2-13, vol. 18, Issue 5, IEEE Computer Graphics and Applications.

Fisher et al., "Virtual Environment Display System", ACM Workshop on Interactive 3D Graphics, Oct. 1986, Chapel Hill, NC.

"Virtual High Anxiety", Tech Update, Aug. 1995, pp. 22.

Sheridan et al., "Virtual Reality Check", Technology Review, Oct. 1993, pp. 22-28, vol. 96, No. 7.

Stevens, "Flights into Virtual Reality Treating Real World Disorders", The Washington Post, Mar. 27, 1995, Science Psychology, 2 pages.

"Simulation and Training", 1994, Division Incorporated.

Fletcher, Andrew, EyeToy: "Kinetic Combat—Review," http://www.gamecritics.com/node/3775, 2007, printed from the Internet on Jan. 24, 2011, 4 pages.

Davis, James et al., "Virtual PAT: A Virtual Personal Aerobics Trainer," MIT Media Lab, 1998, 6 pages.

"Virtual PAT: A Virtual Personal Aerobics Trainer—Microsoft Academic Search," http://academic.research.microsoft.com/Paper/350476.aspx, printed from the Internet on Jan. 10, 2011, 2 pages.

Wang, Yong et al., "Using Human Body Gestures as Inputs for Gaming Via Depth Analysis," IEEE International Conference on Multimedia & Expo, 2008, pp. 993-996.

* cited by examiner

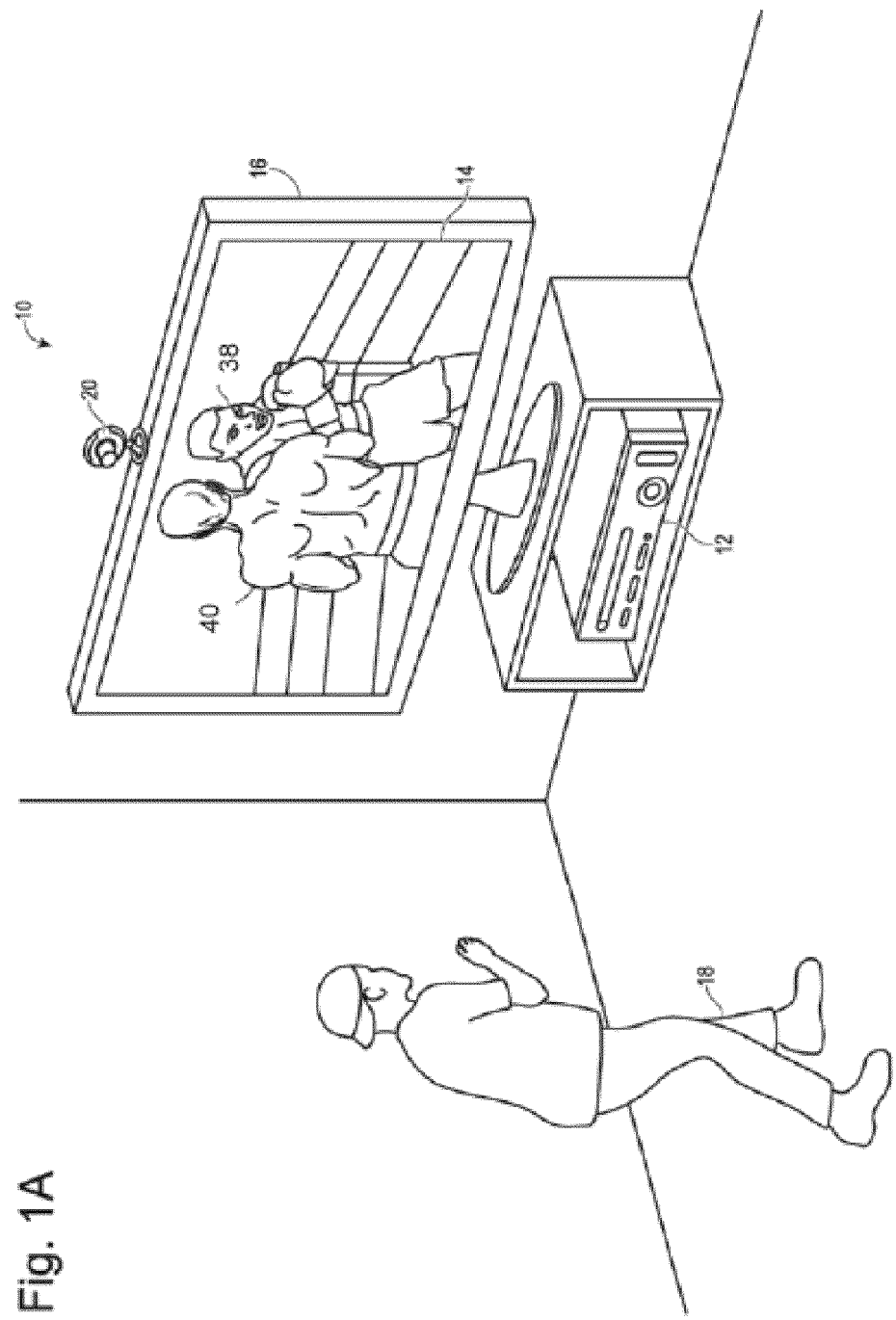

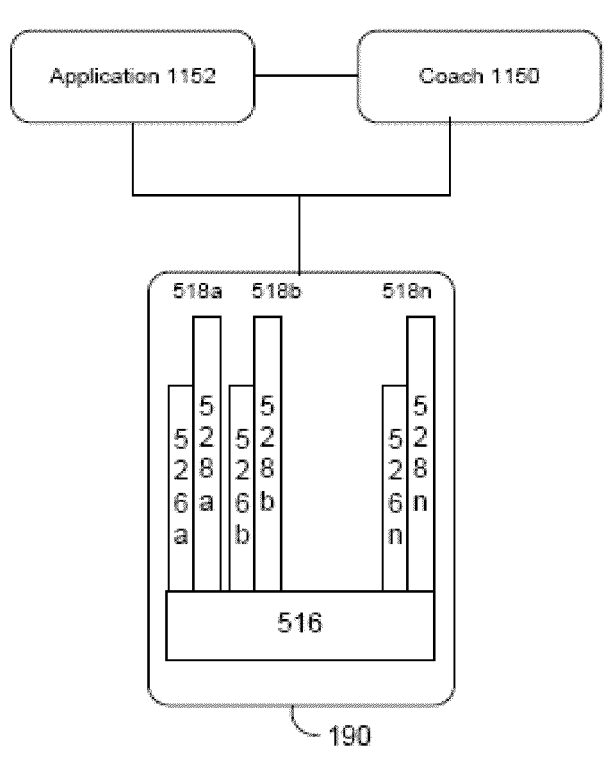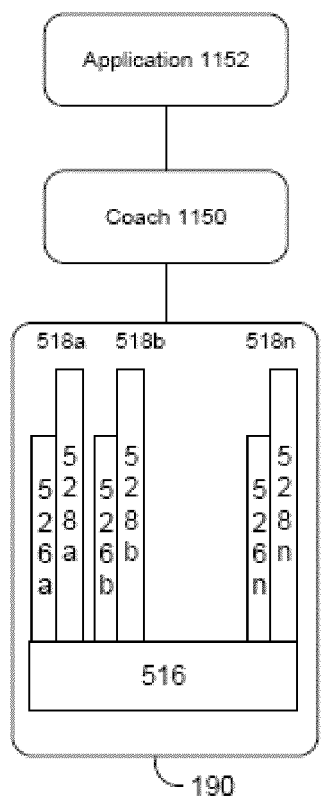
FIG. 11B  FIG. 11C

GESTURE COACH

BACKGROUND OF THE INVENTION

Many computing applications such as computer games, multimedia applications, office applications or the like use controls to allow users to manipulate game characters or other aspects of an application. Typically such controls are input using, for example, controllers, remotes, keyboards, mice, or the like. Unfortunately, such controls can be difficult to learn, thus creating a barrier between a user and such games and applications. Furthermore, such controls may be different than actual game actions or other application actions for which the controls are used. For example, a game control that causes a game character to swing a baseball bat may not correspond to an actual motion of swinging the baseball bat.

SUMMARY OF THE INVENTION

In some systems, a display device may display a model that maps to user motions that have been captured by the system. For example, the model may be displayed as an avatar on a screen, where that avatar's motion can be controlled by mapping the avatar's motion in an application space to the user's motions in the physical space. A user may be unfamiliar with a system that maps the user's motions. For example, the user may not know what gestures are applicable for an executing application. In some cases, a user will not understand or know how to perform the gestures that are applicable for the executing application. A written or pictoral description in a handbook may be insufficient to teach a user how to properly gesture.

Disclosed herein are systems and methods for gesture coaching. As the user attempts to make gestures, captured user data and output from gesture filters corresponding to that captured user data may be analyzed to determine that the user is attempting, but failing, to perform a gesture, and that providing assistance to the user is appropriate. This assistance may comprise teaching the user the proper way to perform the gesture. For example, where the output to a filter comprises a confidence level that the corresponding gesture was performed, and that confidence level is below a recognition threshold, it may be determined that assistance is appropriate to teach the user to perform the gesture in such a way that the corresponding confidence level is at or above that recognition threshold.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The systems, methods, and computer readable media for gesture coaching, in accordance with this specification, are further described with reference to the accompanying drawings in which:

FIGS. 1A and 1B illustrate an example embodiment of a target recognition, analysis, and tracking system with a user playing a game.

FIGS. 11B and 11C depict example architectures for gesture coaching integrated with a gesture recognizer engine and an application.

DETAILED DESCRIPTION OF ILLUSTRATIVE EMBODIMENTS

Figure 1B:
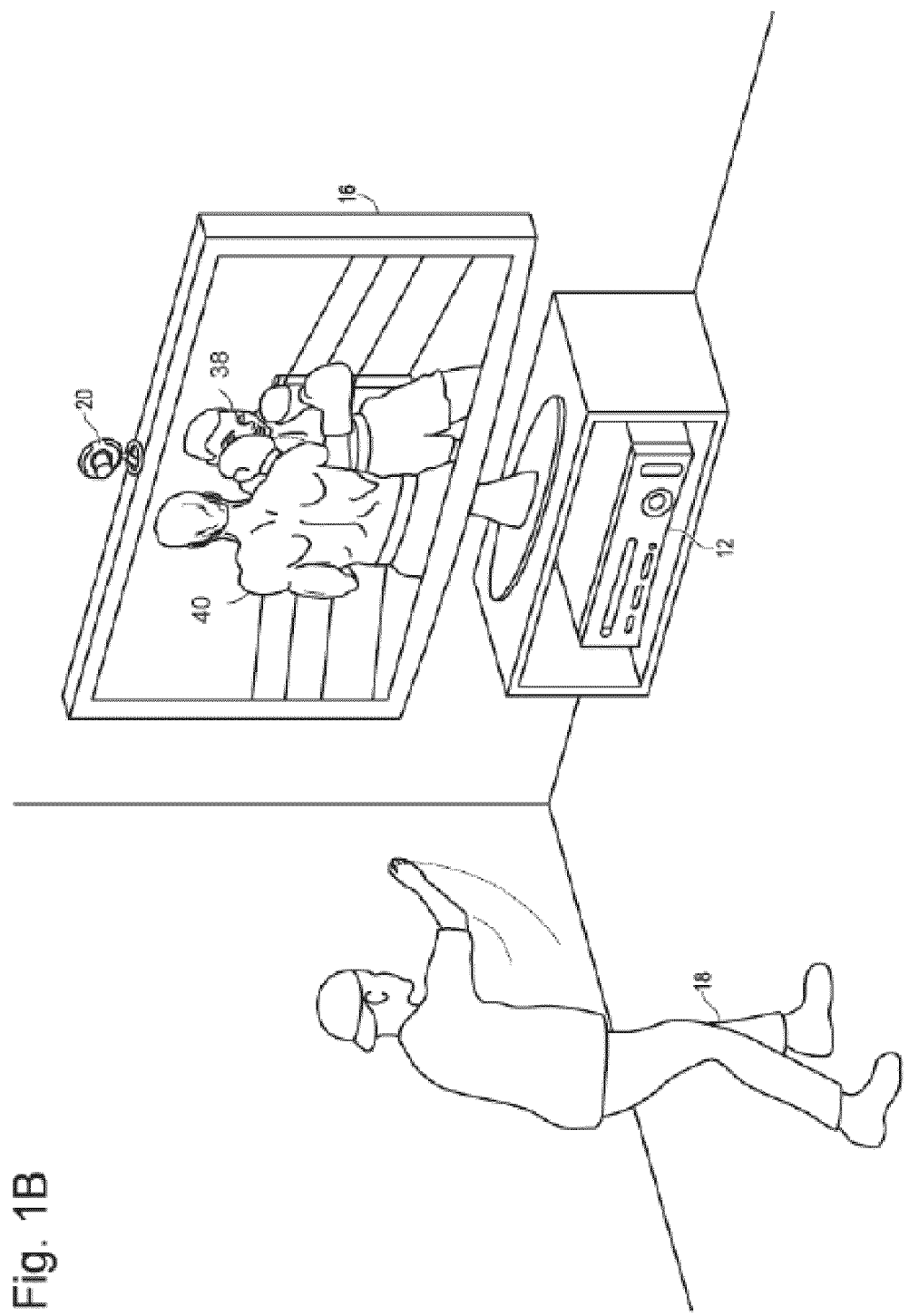

As will be described herein, a user may control an application executing on a computing environment such as a game console, a computer, or the like by performing one or more gestures. Disclosed herein are systems and methods for demonstrating motions for desired gestures to the user. For example, the computing environment may provide visual assistance to train a user how to make the appropriate motions applicable to an executing application.

To generate models representative of a target or object in a physical space, a capture device can capture a depth image of the physical space and scan targets in the scene. A target may include humans or other objects in the scene. In one embodiment, the capture device may determine whether one or more targets in the scene corresponds to a human target such as the user. To determine whether a target in the scene corresponds to a human target, each of the targets may be flood filled and compared to a pattern of a human body model. A target identified as a human may be scanned to generate a skeletal model associated therewith. The skeletal model may then be provided to a computing environment for tracking the skeletal model and rendering an avatar associated with the skeletal model. The computing environment may map the motions of the user in the physical space to a visual representation on a display device, such as an avatar. The computing environment may determine which controls to perform in an application executing on the computer environment based on, for example, gestures of the user that have been recognized and mapped to the skeletal model. Thus, user assistance may be displayed, such as via an avatar on a screen, and the user can control that avatar's motion and execute controls of the operating system or executing application, for example, by making gestures in the physical space.

It may be desirable in some situations to provide visual assistance to teach a user how to gesture properly to control the executing application. For example, the user may not be aware of, or know how to perform, the motions that correspond to a particular gesture that is applicable to the executing application. The system may detect errors in the user's gestures, indicating that the user needs training to properly gesture.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

The system, methods, and components of providing visual training assistance as described herein may be embodied in a multi-media console, such as a gaming console, or in any other computing device in which it is desired to provide visual assistance, by way of example and without any intended limitation, satellite receivers, set top boxes, arcade games, personal computers (PCs), portable telephones, personal digital assistants (PDAs), and other hand-held devices.

FIGS. 1A and 1B illustrate an example embodiment of a configuration of a target recognition, analysis, and tracking system 10 with a user 18 playing a boxing game. In an example embodiment, the system 10 may recognize, analyze, and/or track a human target such as the user 18. The system 10 may gather information related to the user's gestures in the physical space.

The system 10 may provide visual assistance to a user to demonstrate desired gestures. The provision of the visual assistance may be triggered in a number of ways. For example, the system may detect an error in the user's motion or a deviation from an expected motion. The detection of such error or deviation may trigger visual assistance that demonstrates the desired gesture. In another example, the executing application may provide visual assistance for training purposes to demonstrate the appropriate motions for control. Assistance may take a variety of forms such as tactile, auditory and visual. In an embodiment, the assistance consists of an audio assistance, visual assistance, changing the color of a display element, lining of a display element, fading of a display element, strobing of a display element, a tracer pattern of some combination of these forms of assistance.

As shown in FIG. 1A, the target recognition, analysis, and tracking system 10 may include a computing environment 12. The computing environment 12 may be a computer, a gaming system or console, or the like. According to an example embodiment, the computing environment 12 may include hardware components and/or software components such that the computing environment 12 may be used to execute applications such as gaming applications, non-gaming applications, or the like.

As shown in FIG. 1A, the target recognition, analysis, and tracking system 10 may further include a capture device 20. The capture device 20 may be, for example, a camera that may be used to visually monitor one or more users, such as the user 18, such that gestures performed by the one or more users may be captured, analyzed, and tracked to perform one or more controls or actions within an application, as will be described in more detail below.

According to one embodiment, the target recognition, analysis, and tracking system 10 may be connected to an audiovisual device 16 such as a television, a monitor, a high-definition television (HDTV), or the like that may provide game or application visuals and/or audio to a user such as the user 18. For example, the computing environment 12 may include a video adapter such as a graphics card and/or an audio adapter such as a sound card that may provide audiovisual signals associated with the game application, non-game application, or the like. The audiovisual device 16 may receive the audiovisual signals from the computing environment 12 and may then output the game or application visuals and/or audio associated with the audiovisual signals to the user 18. According to one embodiment, the audiovisual device 16 may be connected to the computing environment 12 via, for example, an S-Video cable, a coaxial cable, an HDMI cable, a DVI cable, a VGA cable, or the like.

As shown in FIGS. 1A and 1B, the target recognition, analysis, and tracking system 10 may be used to recognize, analyze, and/or track a human target such as the user 18. For example, the user 18 may be tracked using the capture device 20 such that the movements of user 18 may be interpreted as controls that may be used to affect the application being executed by computer environment 12. Thus, according to one embodiment, the user 18 may move his or her body to control the application.

As shown in FIGS. 1A and 1B, in an example embodiment, the application executing on the computing environment 12 may be a boxing game that the user 18 may be playing. For example, the computing environment 12 may use the audiovisual device 16 to provide a visual representation of a boxing opponent 38 to the user 18. The computing environment 12 may also use the audiovisual device 16 to provide a visual representation of a player avatar 40 that the user 18 may control with his or her movements. For example, as shown in FIG. 1B, the user 18 may throw a punch in physical space to cause the player avatar 40 to throw a punch in game space. Thus, according to an example embodiment, the computer environment 12 and the capture device 20 of the target recognition, analysis, and tracking system 10 may be used to recognize and analyze the punch of the user 18 in physical space such that the punch may be interpreted as a game control of the player avatar 40 in game space.

Other movements by the user 18 may also be interpreted as other controls or actions, such as controls to bob, weave, shuffle, block, jab, or throw a variety of different power punches. Furthermore, some movements may be interpreted as controls that may correspond to actions other than controlling the player avatar 40. For example, the player may use movements to end, pause, or save a game, select a level, view high scores, communicate with a friend, etc.

As described in more detail below, the system 10 may provide visual assistance to the user 18 to demonstrate gestures that are applicable to the executing application. In an example embodiment, the visual assistance is prerecorded content in the form of a skeletal representation, a ghosted image, or a player avatar. In another example embodiment, live content may be presented to the user.

In example embodiments, the human target such as the user 18 may have an object. In such embodiments, the user of an electronic game may be holding the object such that the motions of the player and the object may be used to adjust and/or control parameters of the game. For example, the motion of a player holding a racket may be tracked and utilized for controlling an on-screen racket in an electronic sports game. In another example embodiment, the motion of a player holding an object may be tracked and utilized for controlling an on-screen weapon in an electronic combat game. The system 10 may provide visual assistance for demonstrating the gestures related to the user's motion with respect to the object the player is holding in the physical space and/or in the application space.

According to other example embodiments, the target recognition, analysis, and tracking system 10 may further be used to interpret target movements as operating system and/or application controls that are outside the realm of games. For example, virtually any controllable aspect of an operating system and/or application may be controlled by movements of the target such as the user 18. And the system 10 may provide visual assistance for demonstrating the gestures related to any controllable aspect of the operating system and/or application.

Figure 2:
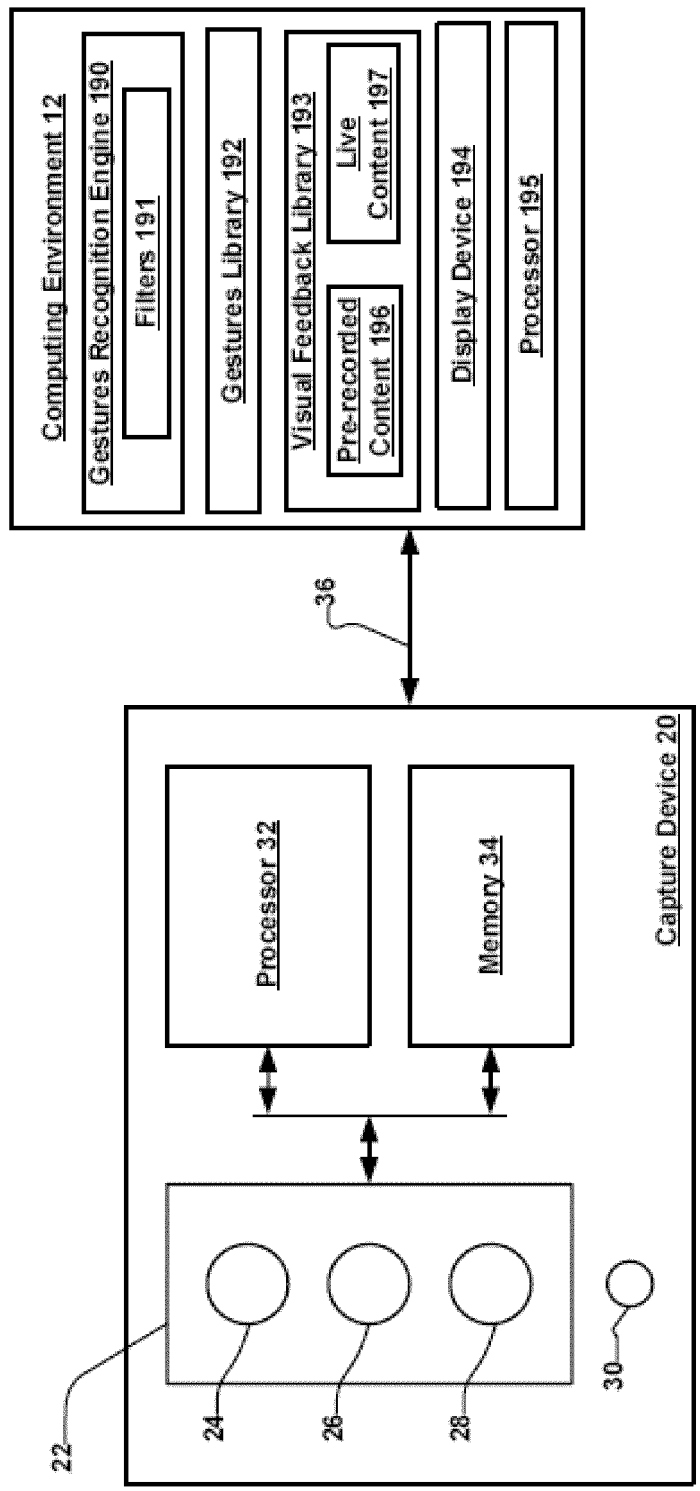
FIG. 2 illustrates an example embodiment of a capture device that may be used in a target recognition, analysis, and tracking system and incorporate gesture coaching.

FIG. 2 illustrates an example embodiment of the capture device 20 that may be used in the target recognition, analysis, and tracking system 10. According to an example embodiment, the capture device 20 may be configured to capture video with depth information including a depth image that may include depth values via any suitable technique including, for example, time-of-flight, structured light, stereo image, or the like. According to one embodiment, the capture device 20 may organize the calculated depth information into "Z layers," or layers that may be perpendicular to a Z axis extending from the depth camera along its line of sight.

As shown in FIG. 2, the capture device 20 may include an image camera component 22. According to an example embodiment, the image camera component 22 may be a depth camera that may capture the depth image of a scene or an RGB camera 28 that may capture the color from the scene. The depth image may include a two-dimensional (2-D) pixel area of the captured scene where each pixel in the 2-D pixel area may represent a length in, for example, centimeters, millimeters, or the like of an object in the captured scene from the camera.

As shown in FIG. 2, according to an example embodiment, the image camera component 22 may include an IR light component 24, a three-dimensional (3-D) camera 26, and an RGB camera 28 that may be used to capture the depth image of a scene. For example, in time-of-flight analysis, the IR light component 24 of the capture device 20 may emit an infrared light onto the scene and may then use sensors (not shown) to detect the backscattered light from the surface of one or more targets and objects in the scene using, for example, the 3-D camera 26 and/or the RGB camera 28. In some embodiments, pulsed infrared light may be used such that the time between an outgoing light pulse and a corresponding incoming light pulse may be measured and used to determine a physical distance from the capture device 20 to a particular location on the targets or objects in the scene. Additionally, in other example embodiments, the phase of the outgoing light wave may be compared to the phase of the incoming light wave to determine a phase shift. The phase shift may then be used to determine a physical distance from the capture device to a particular location on the targets or objects.

According to another example embodiment, time-of-flight analysis may be used to indirectly determine a physical distance from the capture device 20 to a particular location on the targets or objects by analyzing the intensity of the reflected beam of light over time via various techniques including, for example, shuttered light pulse imaging.

In another example embodiment, the capture device 20 may use a structured light to capture depth information. In such an analysis, patterned light (i.e., light displayed as a known pattern such as grid pattern or a stripe pattern) may be projected onto the scene via, for example, the IR light component 24. Upon striking the surface of one or more targets or objects in the scene, the pattern may become deformed in response. Such a deformation of the pattern may be captured by, for example, the 3-D camera 26 and/or the RGB camera 28 and may then be analyzed to determine a physical distance from the capture device to a particular location on the targets or objects.

According to another embodiment, the capture device 20 may include two or more physically separated cameras that may view a scene from different angles, to obtain visual stereo data that may be resolved to generate depth information The capture device 20 may further include a microphone 30. The microphone 30 may include a transducer or sensor that may receive and convert sound into an electrical signal. According to one embodiment, the microphone 30 may be used to reduce assistance between the capture device 20 and the computing environment 12 in the target recognition, analysis, and tracking system 10. Additionally, the microphone 30 may be used to receive audio signals that may also be provided by the user to control applications such as game applications, non-game applications, or the like that may be executed by the computing environment 12.

In an example embodiment, the capture device 20 may further include a processor 32 that may be in operative communication with the image camera component 22. The processor 32 may include a standardized processor, a specialized processor, a microprocessor, or the like that may execute instructions that may include instructions for receiving the depth image, determining whether a suitable target may be included in the depth image, converting the suitable target into a skeletal representation or model of the target, or any other suitable instruction.

The capture device 20 may further include a memory component 34 that may store the instructions that may be executed by the processor 32, images or frames of images captured by the 3-D camera or RGB camera, or any other suitable information, images, or the like. According to an example embodiment, the memory component 34 may include random access memory (RAM), read only memory (ROM), cache, Flash memory, a hard disk, or any other suitable storage component. As shown in FIG. 2, in one embodiment, the memory component 34 may be a separate component in communication with the image capture component 22 and the processor 32. According to another embodiment, the memory component 34 may be integrated into the processor 32 and/or the image capture component 22.

As shown in FIG. 2, the capture device 20 may be in communication with the computing environment 12 via a communication link 36. The communication link 36 may be a wired connection including, for example, a USB connection, a Firewire connection, an Ethernet cable connection, or the like and/or a wireless connection such as a wireless 802.11b, g, a, or n connection. According to one embodiment, the computing environment 12 may provide a clock to the capture device 20 that may be used to determine when to capture, for example, a scene via the communication link 36.

Additionally, the capture device 20 may provide the depth information and images captured by, for example, the 3-D camera 26 and/or the RGB camera 28, and a skeletal model that may be generated by the capture device 20 to the computing environment 12 via the communication link 36. The computing environment 12 may then use the skeletal model, depth information, and captured images to, for example, recognize user gestures and in response control an application such as a game or word processor. For example, as shown, in FIG. 2, the computing environment 12 may include a gesture recognition engine 190 and a gestures library 192 containing one or more gesture filters 191.

Each filter 191 may comprise information defining a gesture along with parameters, or metadata, for that gesture. The data captured by the cameras 26, 28 and device 20 in the form of the skeletal model and movements associated with it may be compared to the gesture filters in the gesture library 192 to identify when a user (as represented by the skeletal model) has performed one or more gestures. Inputs to a filter such as filter 191 may comprise things such as joint data about a user's joint position, like angles formed by the bones that meet at the joint, RGB color data from the scene, and the rate of change of an aspect of the user.

For instance, a throw, which comprises motion of one of the hands from behind the rear of the body to past the front of the body, may be implemented as a gesture filter comprising information representing the movement of one of the hands of the user from behind the rear of the body to past the front of the body, as that movement would be captured by a depth camera. Image data from the scene may also be captured from an RGB camera. As mentioned, parameters may be set for the gesture. Where the gesture is a throw, a parameter may be a threshold velocity that the hand has to reach, a distance the hand must travel (either absolute, or relative to the size of the user as a whole), and a confidence rating by the recognizer engine that the gesture occurred. These parameters for the gesture may vary between applications, between contexts of a single application, or within one context of one application over time.

Outputs from a filter 191 may comprise things such as the confidence that a given gesture is being made, the speed at which a gesture motion is made, and a time at which a gesture motion is made. The gestures may be associated with various controls of an application. Thus, the computing environment 12 may use the gesture recognizer engine 190 to interpret movements of the skeletal model and to control an application based on the movements.

In an embodiment, a gesture filter comprises an algorithm that accepts one or more pieces of data regarding the user as input, and returns one or more outputs regarding the corresponding gesture. For instance, a "user height" gesture filter algorithm may take a skeletal map of a user as input, process that data, and return an output of the height of the user as calculated by the algorithm.

The computing environment 12 may include a processor 195 that can process the depth image to determine what objects are in a scene, such as a user 18 or an object in the room. This can be done, for instance, by grouping together of pixels of the depth image that share a similar distance value. The image may also be parsed to produce a skeletal representation of the user, where features, such as joints and tissues that run between joints is identified. There exist skeletal mapping techniques to capture a person with a depth camera and from that determine various spots on that user's skeleton, joints of the hand, wrists, elbows, knees, nose, ankles, shoulders, and where the pelvis meets the spine. Other techniques include transforming the image into a body model representation of the person and transforming the image into a mesh model representation of the person.

In an embodiment, the processing is performed on the capture device 20 itself, and the raw image data of depth and color (where the capture device comprises a 3D camera) values are transmitted to the computing environment 12 via link 36. In another embodiment, the processing is performed by a processor 32 coupled to the camera 402 and then the parsed image data is sent to the computing environment 12. In still another embodiment, both the raw image data and the parsed image data are sent to the computing environment 12. The computing environment 12 may receive the parsed image data but it may still receive the raw data for executing the current process or application. For instance, if an image of the scene is transmitted across a computer network to another user, the computing environment 12 may transmit the raw data for processing by another computing environment.

The computing environment 12 may use the gestures library 192 to interpret movements of the skeletal model and to control an application based on the movements. The computing environment 12 can model and display a representation of a user, such as in the form of an avatar or a pointer on a display, such as on a display device 194. Display device 194 may include a computer monitor, a television screen, or any suitable display device. For example, a camera-controlled computer system may capture user image data and display user assistance on a television screen that maps to the user's gestures. The user assistance may be displayed as an avatar on the screen such as shown in FIGS. 1A and 1B.

Figure 8A:
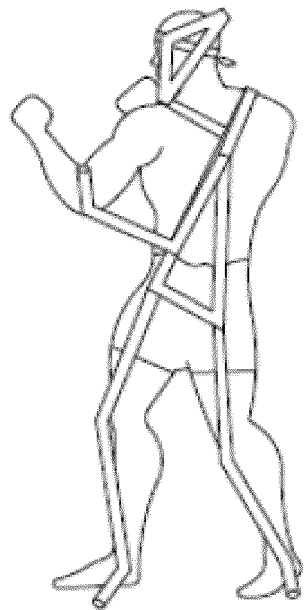
FIG. 8A illustrates an example display of visual assistance superimposed on a visual representation of a user's gestures.
Figure 8B:
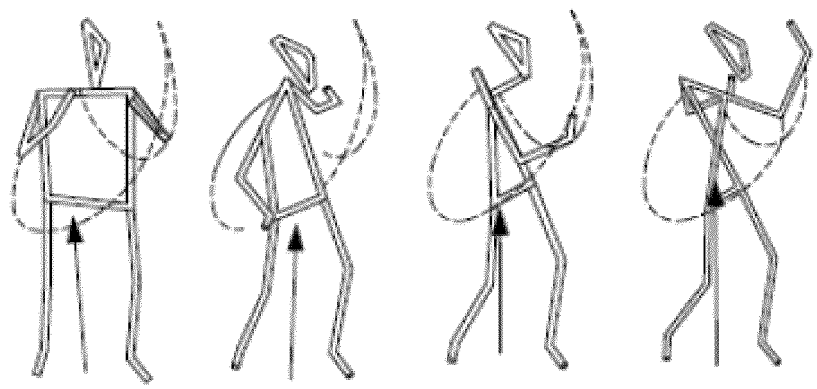
FIG. 8B illustrates an example display of visual assistance that comprises a demonstration of a gesture.
Figure 9:
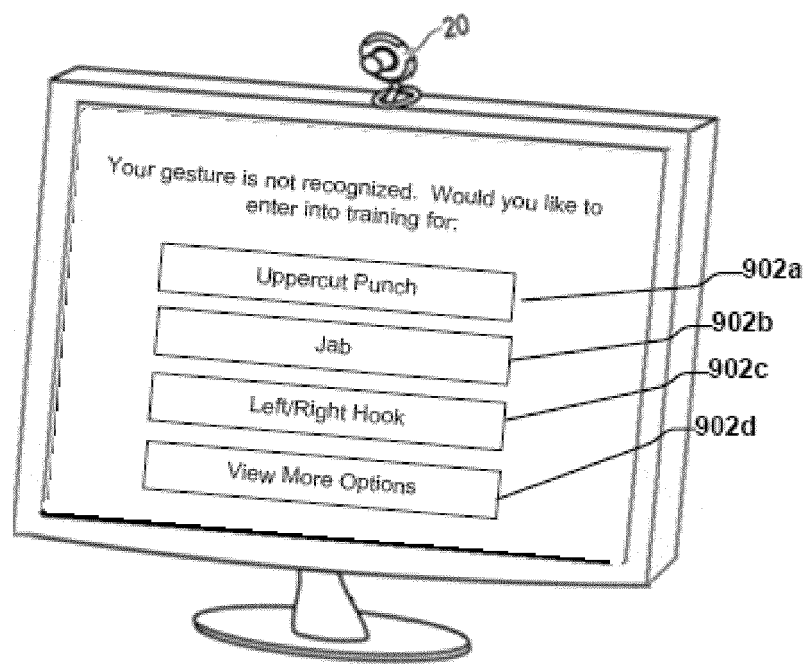
FIG. 9 illustrates an example display of options for entering into a training mode to receive visual assistance.
Figure 10:
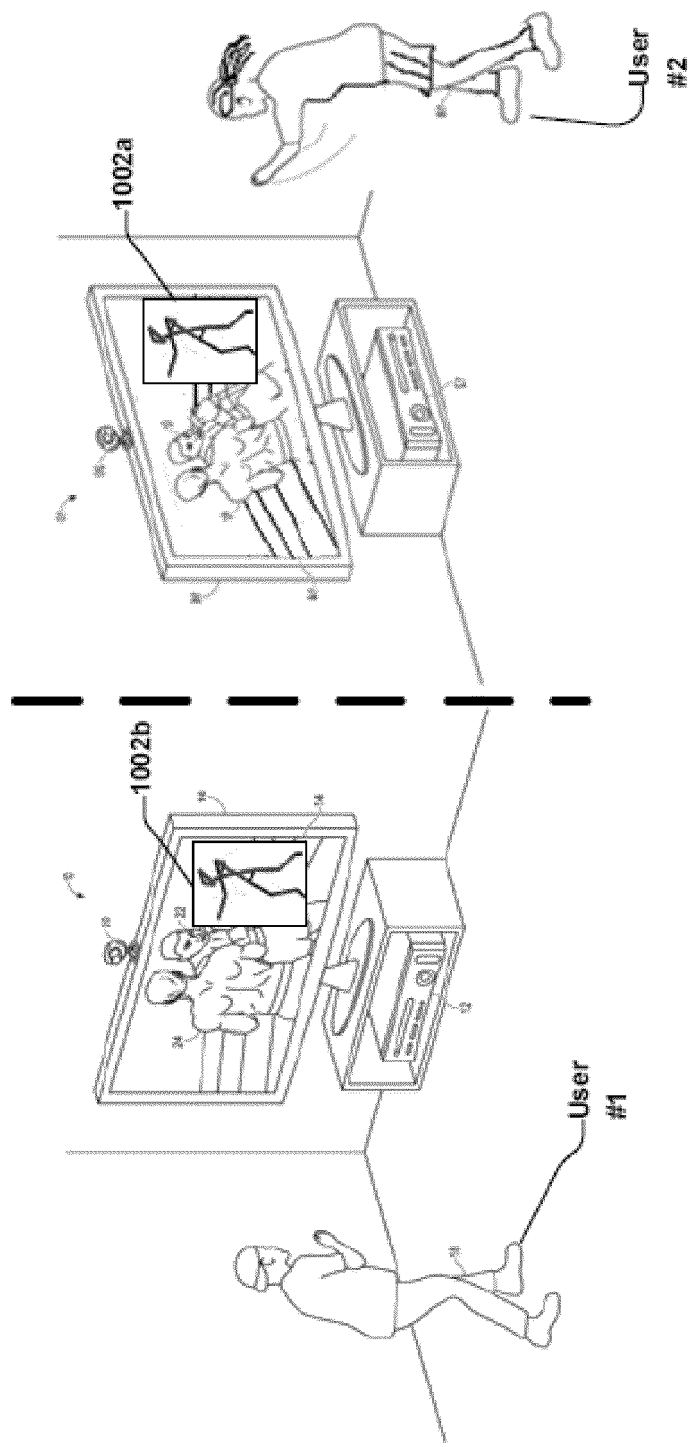
FIG. 10 illustrates remote users interacting over a network connection, where visual assistance of one user's motion is provided to the second user.

The visual assistance library 193 may comprise information related to the visual assistance for a collection of gestures. The visual assistance library 193 may provide information to the display device 194 for the display of a visual representation of instructional gesture data. For example, the display device may display a skeletal representation, a ghosted image, or a player avatar that can demonstrate a gesture. As described in more detail below, FIGS. 7A-7D illustrate both the user assistance and the visual assistance comprising instructional gesture data, shown side by side. FIG. 8A illustrates an example display of visual assistance superimposed on a visual representation of a user's gestures. FIG. 8B illustrates an example display of visual assistance that comprises a demonstration of a gesture. FIG. 9 illustrates an example display of options for entering into a training mode to receive visual assistance. FIG. 10 illustrates remote users interacting over a network connection, where one user provides live visual assistance to the second user.

Various events may trigger the display of visual assistance for gesture demonstration. The system may detect errors in the user's motion, the user's motion may not correspond to a recognized gesture, the user may request training to learn a particular gesture, etc. An analysis of the user's motion may trigger the application to provide visual assistance to the user, or an option to view visual assistance, to teach the proper motion for, for example, throwing gestures recognized by the application. As described, the visual assistance may be in the form of a skeletal representation that demonstrates, for example, the proper overhand throwing gesture. The parameters and error identifiers for the gesture may vary between applications, between contexts of a single application, or within one context of one application over time.

The visual assistance information may be provided for training, correcting, modifying, or teaching a user to properly move in the physical space, to trigger a particular motion, or to properly move for success in the application. For example, the user may be playing a boxing game. The computing environment 12 may identify a gesture that is applicable to the executing application, such as an uppercut punch, and direct the display device 194 to provide the visual assistance comprising instructions for how to perform the uppercut punch. The visual assistance could be an avatar on a screen that demonstrates the proper motion for the uppercut punch.

A gesture filter 191 in the gestures library 192 that can recognize, track, or identify a gesture may also identify when visual assistance should be provided. For instance, where the gesture is an overhand throw, the data captured by the cameras 26, 28 and device 20 in the form of the skeletal model and movements associated with it may be compared to the gesture filters in the gesture library 192. An output of a filter may be the identification that the user (as represented by the skeletal model) is performing an overhand throwing gesture. An overhand throw, which comprises motion of one of the hands from behind the rear of the body to past the front of the body, may be implemented as a gesture filter comprising information representing the movement of one of the hands of the user from behind the rear of the body to past the front of the body, as that movement would be captured by a depth camera.

The variation between the user's gestures and the parameters set in the filter for an overhand throwing gesture may indicate a failure in the user's gesture and trigger entry into a training mode to teach the user the proper motion. The detection of an error or a change in the identified gesture based on filter parameters may trigger the display of visual assistance. Parameters may be set for an overhand throw that assist in identifying errors in the user's gesture. For example, the system may be executing a baseball game application. An overhand throwing gesture may have as a parameter a volume of space in which the user's arm should move. If a gesture filter 191 identifies, in the identified overhand throwing motion, that the user's arm has traveled outside the volume of space, this may be indicative of an error in the user's motion rather than a transition to a different gesture. The application may be expecting an overhand throwing gesture because the game is at a point where the user is pitching to a batter. The failure to recognize the user's gestures as the expected overhand throwing gesture may trigger the display of visual assistance. The gesture filter may not recognize the gesture as an overhand throwing gesture anymore because the motion no longer meets the parameters for an overhand throw, but instead meets the filter parameters for a different gesture, such as an underhand throwing motion. An unexpected transition between different gestures may trigger the display of visual assistance.

As mentioned, parameters may be set for a gesture. For example, where the gesture is a throw, a parameter may be a threshold velocity that the hand has to reach, a distance the hand must travel (either absolute, or relative to the size of the user as a whole), and a confidence rating by the recognizer engine that the gesture occurred. Various thresholds and ranges may be set for the parameters that indicate an error in the user's gesture. For example, the volume of space through which a user's arm should move could vary in size depending on the skill level of the user.

The parameters that correspond to each gesture may vary based on a user's performance, the executing application, a context, a skill level, or the like. For example, a parameter for an overhand football throw in a "beginner" skill level may comprise a larger volume of space through which the hand can travel such that the system associates the gesture with an overhand throw and processes it accordingly. By varying certain parameters associated with a gesture, the system can accommodate less experienced players.

Several possible gestures may correspond to the user's gesture. For example, a user's gesture measured in the physical space may meet the criteria of several filters, each comprising parameters for possible gestures. The variations between the data representative of the measured gesture and the filter parameters for possible gestures may indicate a failure in the execution of the measured gesture.

If the data representative of the user's gesture does not correspond to any filter parameters for possible gestures, it is likely that the user is not performing the gesture properly as it relates to the executing application. It may be desirable to trigger a training session for a user if the user's gestures are not registering as one of the possible gestures.

The system can predict the intention of the user's gesture if the user's gesture does not correspond to any filter data. The system may predict an intended gesture based on what gesture would be applicable for the executing application at that point in time. The prediction may be based on a comparison of the data representative of the measured gesture and the filter parameters and identifying the gesture(s) with parameters that more closely match the measured gesture data.

Variations between the data representative of the measured gesture and the filter parameters for possible gestures may indicate a failure in the execution of the measured gesture. The variation can be compared to a threshold level of acceptance, where a variance amount that is below the threshold may trigger visual assistance with instructional gesture data. The threshold level of acceptance could be related to the confidence rating. As described above, outputs from a filter may comprise things such as the confidence that a given gesture is being made. A low confidence rating may be an indication that a user is not gesturing properly. The threshold level of acceptance may be set based on the confidence rating. For example, if the gesture is identified by the gesture recognizer engine as an overhand throw, and the confidence rating is low, the system may trigger the display of visual assistance with instructional gesture data. Alternately, the system may require a high confidence rating such that there is a higher confidence that the user is attempting the particular gesture. The visual assistance may trigger when variations between the data representative of the measured gesture and filter parameters are below a threshold level of acceptance.

The threshold level of acceptance could be a value set for a certain filter parameter. Each parameter of a filter that represents a gesture could have a threshold level of acceptance. The threshold level of acceptance could be a single threshold value or a range of acceptable values. If a measurement of the user's measured gesture does not meet the threshold level or fall within the acceptable range, it may be desirable to display visual assistance comprising instructional gesture data. For example, the threshold level of acceptance for an overhand throw, as it applies to a pitching motion in a baseball game, may be set as a velocity equal to 25 mph. Thus, if the user's gesture is identified as an overhand throw, the velocity parameter of the filter for an overhand throw may be compared to the velocity of the user's measured gesture. If the user's measured velocity does not meet 25 mph, this may trigger the display of visual assistance to teach the user how to properly motion to reach the proper velocity.

The threshold level of acceptance may be set, modified, or changed depending on the context, a user, the gesture-based system, history data for a user, history data for an application, an identity of improvement, etc. The threshold level could be an acceptable amount of variance from a preferred parameter or from a range of parameter values associated with a possible gesture. The values for a threshold level of acceptance may be based on a user's performance, the executing application, a context, a skill level, or the like. The threshold level of acceptance may be based on a single filter parameter or a plurality of filter parameters for a particular gesture. Similarly, the system can adapt the threshold level of acceptance for a gesture. For example, the threshold levels may be modified over time, changed by a user, the system or an application, for example.

Filter parameters and threshold levels of acceptance may be set such that the triggers for visual assistance are not in excess or are in accordance with user preferences. For example, some users may not want any training assistance or a user may not want to interrupt the executing application for training sessions, but rather select a training mode for instructional purposes. Rather than trigger the visual assistance every time there is a variation from filter data for a gesture, the system may determine whether or not to display the instructional gesture data based on various triggers.

The filter parameters and threshold levels of acceptance for error identification may be modified such that the visual assistance only triggers at useful times. For example, a gesture for an overhand throw may need to be recognized X number of times before assistance will be offered. Thus, the system can monitor a user's motion and not give assistance until a certain number of incorrect or varied motions. That way, it doesn't trigger if one mistake throw is made. But, if the program identifies something the user could change, even if they are executing the gesture with success, the system may provide an option for training For example, if a user's overhand throw is identified, the system may identify that a change to the user's lower body could generate more velocity, or a change in the user's follow-through could create a curve ball motion.

If an inexperienced or beginner user is playing a throwing game, the filter parameters defining the volume of space may be larger allowing a larger margin of error before triggering visual assistance for the gesture. The user may also request that visual assistance be provided when the user is not meeting a particular skill level. The user may request visual assistance to help attain a higher skill level. The threshold of parameters may change depending on the skill level of the user. For example, a volume of space for a punch or an overhand throw may have a larger acceptable margin of error for a beginner player. Thus, the trigger for entering training mode or providing visual assistance may change depending on the parameters of the application, settings selected by the user, the type of training available for the application, etc.

The visual assistance library 193 may comprise modules that provide access to, store, and process visual assistance information for demonstrating a gesture. The visual assistance may be specific to an application, to a user, or to a particular gesture. Some gestures are applicable to a particular application, where the same gesture in another application results in a different control. For example, in one application, waving a hand may be the gesture that represents flying; in another application, holding both arms up and slowly swaying them back in forth may be the gesture that represents flying.

The information related to the visual assistance in the visual assistance library 193 may take any suitable form. In an example embodiment, the visual assistance is in the form of prerecorded content, i.e., content that is recorded during a stage prior to use of that content. The prerecorded content module 196 may record or store prerecorded content that supports the display of a demonstration of a gesture, such as prerecorded audio or visual related to a gesture. The prerecorded content module 196 may provide techniques for connecting to a network and receiving prerecorded gesture information from a remote server or via the computing environment of a networked user. The prerecorded content module 196 can process the prerecorded content to provide visual assistance for the gesture, such as by displaying a skeletal representation, a ghosted image, or a player avatar that demonstrates the gesture.

The prerecorded content may be specific to an application, to a user, to a gesture, or the prerecorded content may be applicable across applications or to a combination of users. The prerecorded content may be gesture information that was packaged in the visual assistance library 193 of a particular application. For example, if the application is a tennis game application, the application may include a visual assistance library with prerecorded gesture information for displaying tennis related gestures.

The prerecorded content may comprise content recorded by a user, where a user selects to record his or her own gestures for reviewing or for later use. For example, a user may be successful in a tennis game with a particular motion and record it such that, at a later time, the user can access the prerecorded content to view the prerecorded gesture. The user may then view his or her own prerecorded gesture for a demonstration of a gesture that the user has had success with in the past. The user may record gesture content that the system can use for demonstrating gestures to inexperienced users. For example, a parent may record his or her own successful gesture for review by a child. The child can later view and practice using the prerecorded gesture to learn the proper motions to make in the physical space.

In another example embodiment, the visual assistance is in the form of live content, i.e., any information related to providing real-time visual assistance of a gesture. A real-time display refers to the display of a visual representation of a gesture or display of visual assistance, wherein the display is simultaneously or almost simultaneously displayed with the performance of the gesture in the physical space. References to real-time include performance, wherein insignificant processing delays result in minimal delay of the display or are not visible at all to the user. Thus, real-time includes any insignificant delays pertaining to the timeliness of data which has been delayed by the time required for automatic data processing.

The live content module 197 may provide techniques for receiving, processing, and transmitting the live content. For example, the live content module 197 may provide techniques for connecting to a network and receiving a live feed containing gesture information from a remote server or from the computing environment of a networked user. The live content module 197 can process the live feed comprising gesture information to display in a real-time demonstration of a gesture. For example, a remote user could demonstrate a gesture, where information related to the remote user's gestures are transmitted over a network and received by a local user's computing environment. The local computing environment could process the live feed, such as via the live content module, and display visual assistance to a local user in real-time. The visual assistance could be a replay or a live representation of the user's gesture, represented via a visual representation of the user. The live content module 197 can display the visual assistance in any suitable manner, such as by displaying a skeletal representation, a ghosted image, or a player avatar that demonstrates the gesture.

The live content may be specific to an application or to a user, or the live content may be applicable across applications or to a combination of users. For example, live customer support may be accessible for a particular application from a remote computing environment, where the live customer support provides a live feed of gesture information. The live content module 197 may receive the live feed and provide visual assistance to a user that represents the gesture in realtime as the user is gesturing.

In another example of live assistance, users may be remotely connected or networked such that multiple users can interact via their respective computing environments. A first user may recognize that a second user, remote to the first, is performing a gesture incorrectly. The first user can provide a demonstration of the gesture to the user via the networked connection. The second user's computing environment, via the live content module 197, for example, may receive information related to the demonstrated gesture and provide visual assistance to the second user. Therefore, a first user can provide live gesture information to a second user to help the second user learn the proper motions to make in the physical space.

The gesture recognizer engine 190, gestures library 192, and visual assistance library 193 may be implemented in hardware, software or a combination of both. For example, the gestures recognition engine 190, gestures library 192, and visual assistance library 193 may be implemented as software that executes on a processor, such as processor 195, of the computing environment, processor 32 of the capture device 20, on processing unit 101 of FIG. 3, or processing unit 259 of FIG. 4.

Figure 3:
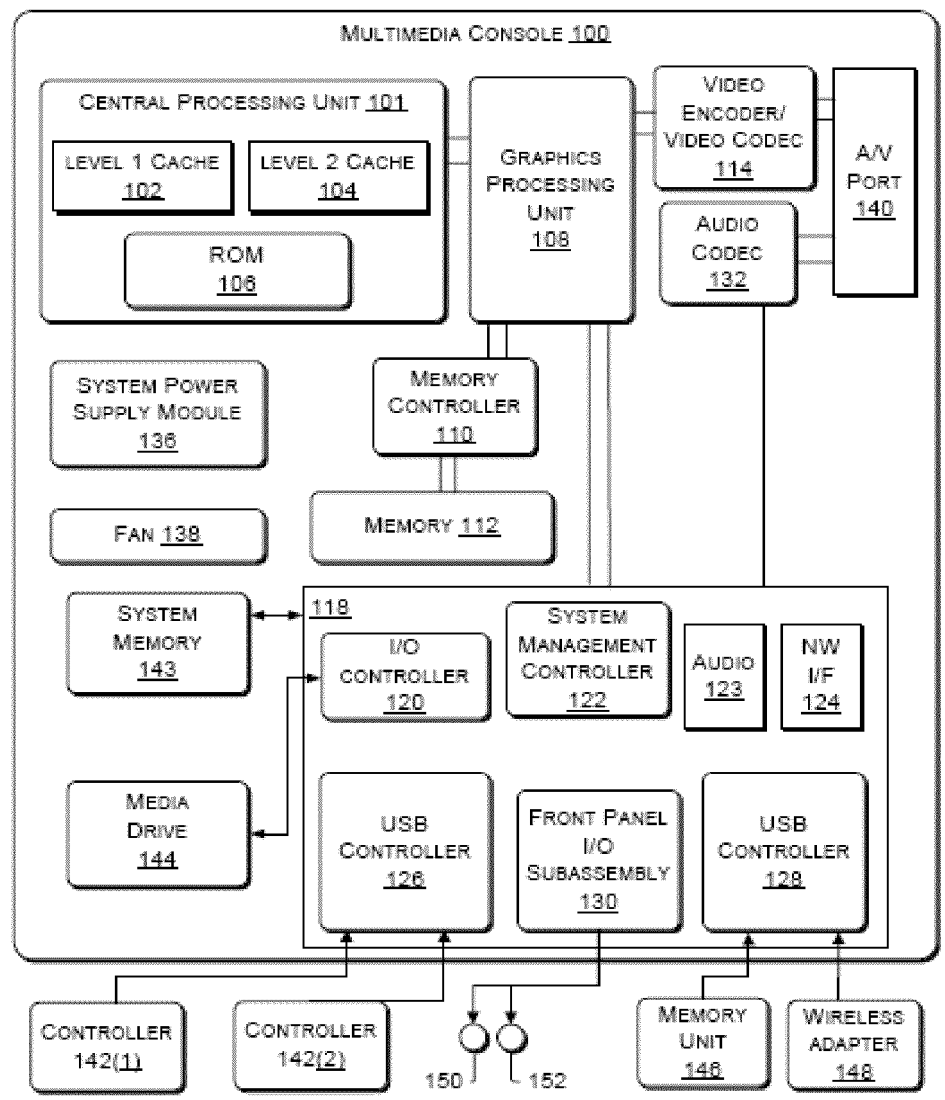
FIG. 3 illustrates another example embodiment of a computing environment in which the techniques disclosed herein for gesture coaching may be embodied.
Figure 4:
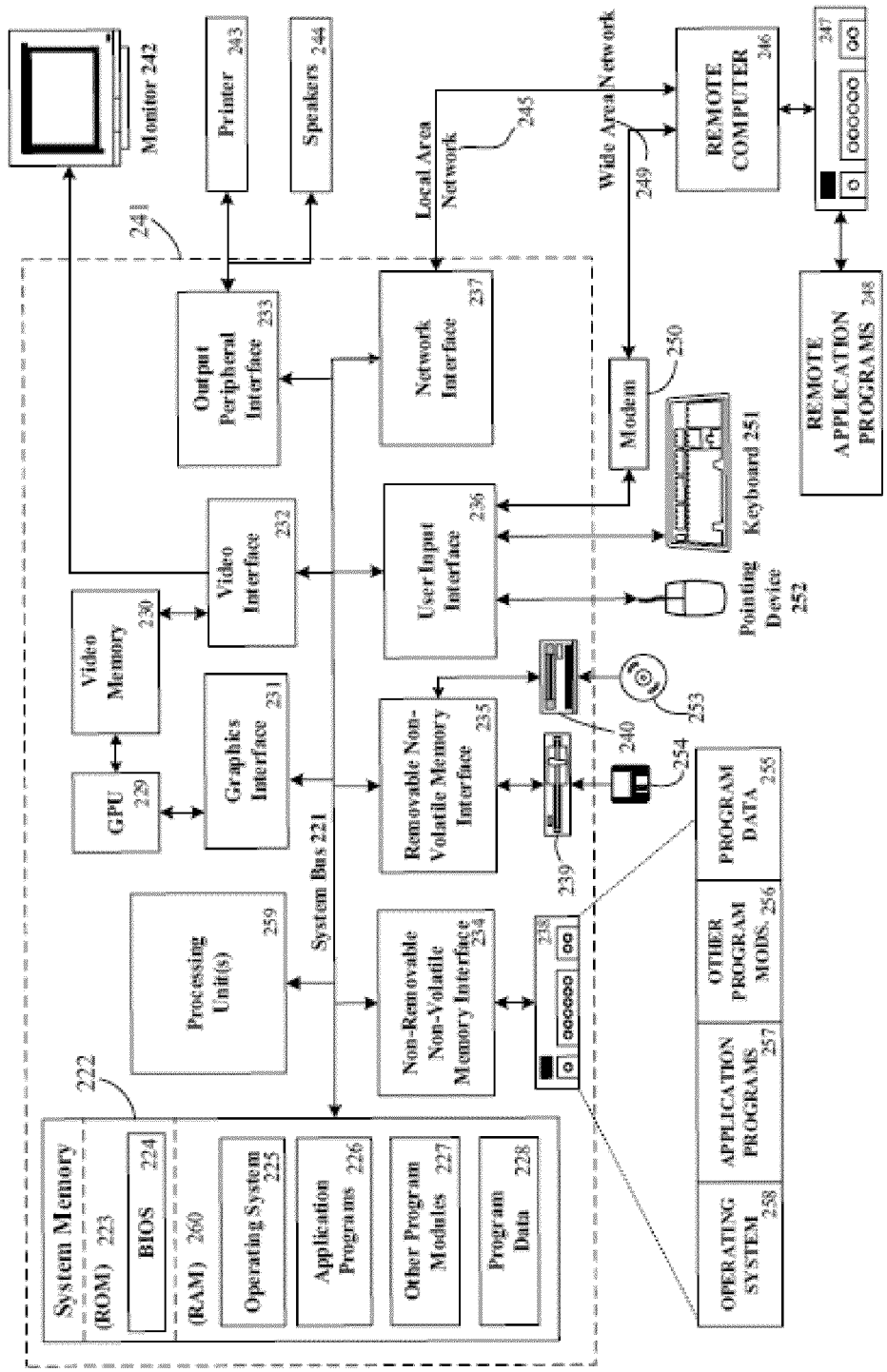
FIG. 4 illustrates another example embodiment of a computing environment in which the techniques disclosed herein for gesture coaching may be embodied.

It is emphasized that the block diagram depicted in FIGS. 2-4 are exemplary and not intended to imply a specific implementation. Thus, the processor 195 or 32 in FIG. 1, the processing unit 101 of FIG. 3, and the processing unit 259 of FIG. 4, can be implemented as a single processor or multiple processors. Multiple processors can be distributed or centrally located. For example, the gesture recognition engine 190 may be implemented as software that executes on the processor 32 of the capture device and the gestures library and visual assistance library 193 may be implemented as software that executes on the processor 195 in the computing environment. Any combination of processors that are suitable for performing the techniques disclosed herein are contemplated. Multiple processors can communicate wirelessly, via hard wire, or a combination thereof FIG. 2 depicts the capture device 20 and the computing environment 12 separately, but it is contemplated that a system comprising any number of devices can perform the functionality shown in FIG. 2. For example, the computing environment may be incorporated into the capture device 20 such that the capture device can function as a single unit with one or more processors. Thus, while the computing environment 12 and capture device 20 are described separately herein, this is for illustration purposes. Any suitable device, system, or combination of devices and systems that can perform the disclosed techniques may be used.

FIG. 3 illustrates an example embodiment of a computing environment that may be used to implement the computing environment 12 of FIG. 2 to interpret one or more gestures in a target recognition, analysis, and tracking system. As shown in FIG. 3, the computing environment may be a multimedia console 100, such as a gaming console. As further shown in FIG. 3, the multimedia console 100 has a central processing unit (CPU) 101 having a level 1 cache 102, a level 2 cache 104, and a flash ROM (Read Only Memory) 106. The level 1 cache 102 and a level 2 cache 104 temporarily store data and hence reduce the number of memory access cycles, thereby improving processing speed and throughput. The CPU 101 may be provided having more than one core, and thus, additional level 1 and level 2 caches 102 and 104. The flash ROM 106 may store executable code that is loaded during an initial phase of a boot process when the multimedia console 100 is powered ON.

A graphics processing unit (GPU) 108 and a video encoder/video codec (coder/decoder) 114 form a video processing pipeline for high speed and high resolution graphics processing. Data is carried from the graphics processing unit 108 to the video encoder/video codec 114 via a bus. The video processing pipeline outputs data to an A/V (audio/video) port 140 for transmission to a television or other display. A memory controller 110 is connected to the GPU 108 to facilitate processor access to various types of memory 112, such as, but not limited to, a RAM (Random Access Memory).

The multimedia console 100 includes an I/O controller 120, a system management controller 122, an audio processing unit 123, a network interface controller 124, a first USB host controller 126, a second USB controller 128 and a front panel I/O subassembly 130 that are preferably implemented on a module 118. The USB controllers 126 and 128 serve as hosts for peripheral controllers 142(1)-142(2), a wireless adapter 148, and an external memory device 146 (e.g., flash memory, external CD/DVD ROM drive, removable media, etc.). The network interface 124 and/or wireless adapter 148 provide access to a network (e.g., the Internet, home network, etc.) and may be any of a wide variety of various wired or wireless adapter components including an Ethernet card, a modem, a Bluetooth module, a cable modem, and the like.

System memory 143 is provided to store application data that is loaded during the boot process. A media drive 144 is provided and may comprise a DVD/CD drive, hard drive, or other removable media drive, etc. The media drive 144 may be internal or external to the multimedia console 100. Application data may be accessed via the media drive 144 for execution, playback, etc. by the multimedia console 100. The media drive 144 is connected to the I/O controller 120 via a bus, such as a Serial ATA bus or other high speed connection (e.g., IEEE 1394).

The system management controller 122 provides a variety of service functions related to assuring availability of the multimedia console 100. The audio processing unit 123 and an audio codec 132 form a corresponding audio processing pipeline with high fidelity and stereo processing. Audio data is carried between the audio processing unit 123 and the audio codec 132 via a communication link. The audio processing pipeline outputs data to the A/V port 140 for reproduction by an external audio player or device having audio capabilities.

The front panel I/O subassembly 130 supports the functionality of the power button 150 and the eject button 152, as well as any LEDs (light emitting diodes) or other indicators exposed on the outer surface of the multimedia console 100. A system power supply module 136 provides power to the components of the multimedia console 100. A fan 138 cools the circuitry within the multimedia console 100.

The CPU 101, GPU 108, memory controller 110, and various other components within the multimedia console 100 are interconnected via one or more buses, including serial and parallel buses, a memory bus, a peripheral bus, and a processor or local bus using any of a variety of bus architectures. By way of example, such architectures can include a Peripheral Component Interconnects (PCI) bus, PCI-Express bus, etc.

When the multimedia console 100 is powered ON, application data may be loaded from the system memory 143 into memory 112 and/or caches 102, 104 and executed on the CPU 101. The application may present a graphical user interface that provides a consistent user experience when navigating to different media types available on the multimedia console 100. In operation, applications and/or other media contained within the media drive 144 may be launched or played from the media drive 144 to provide additional functionalities to the multimedia console 100.

The multimedia console 100 may be operated as a standalone system by simply connecting the system to a television or other display. In this standalone mode, the multimedia console 100 allows one or more users to interact with the system, watch movies, or listen to music. However, with the integration of broadband connectivity made available through the network interface 124 or the wireless adapter 148, the multimedia console 100 may further be operated as a participant in a larger network community.

When the multimedia console 100 is powered ON, a set amount of hardware resources are reserved for system use by the multimedia console operating system. These resources may include a reservation of memory (e.g., 16 MB), CPU and GPU cycles (e.g., 5%), networking bandwidth (e.g., 8 kbs), etc. Because these resources are reserved at system boot time, the reserved resources do not exist from the application's view.

In particular, the memory reservation preferably is large enough to contain the launch kernel, concurrent system applications and drivers. The CPU reservation is preferably constant such that if the reserved CPU usage is not used by the system applications, an idle thread will consume any unused cycles.

With regard to the GPU reservation, lightweight messages generated by the system applications (e.g., popups) are displayed by using a GPU interrupt to schedule code to render popup into an overlay. The amount of memory required for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV resynch is eliminated.

After the multimedia console 100 boots and system resources are reserved, concurrent system applications execute to provide system functionalities. The system functionalities are encapsulated in a set of system applications that execute within the reserved system resources described above. The operating system kernel identifies threads that are system application threads versus gaming application threads. The system applications are preferably scheduled to run on the CPU 101 at predetermined times and intervals in order to provide a consistent system resource view to the application. The scheduling is to minimize cache disruption for the gaming application running on the console.

When a concurrent system application requires audio, audio processing is scheduled asynchronously to the gaming application due to time sensitivity. A multimedia console application manager (described below) controls the gaming application audio level (e.g., mute, attenuate) when system applications are active.

Input devices (e.g., controllers 142(1) and 142(2)) are shared by gaming applications and system applications. The input devices are not reserved resources, but are to be switched between system applications and the gaming application such that each will have a focus of the device. The application manager preferably controls the switching of input stream, without knowledge the gaming application's knowledge and a driver maintains state information regarding focus switches. The cameras 26, 28 and capture device 20 may define additional input devices for the console 100.

FIG. 4 illustrates another example embodiment of a computing environment 220 that may be used to implement the computing environment 12 shown in FIGS. 1A-2 used to interpret one or more gestures in a target recognition, analysis, and tracking system. The computing system environment 220 is only one example of a suitable computing environment and is not intended to suggest any limitation as to the scope of use or functionality of the presently disclosed subject matter. Neither should the computing environment 220 be interpreted as having any dependency or requirement relating to any one or combination of components illustrated in the exemplary operating environment 220. In some embodiments the various depicted computing elements may include circuitry configured to instantiate specific aspects of the present disclosure. For example, the term circuitry used in the disclosure can include specialized hardware components configured to perform function(s) by firmware or switches. In other examples embodiments the term circuitry can include a general purpose processing unit, memory, etc., configured by software instructions that embody logic operable to perform function(s). In example embodiments where circuitry includes a combination of hardware and software, an implementer may write source code embodying logic and the source code can be compiled into machine readable code that can be processed by the general purpose processing unit. Since one skilled in the art can appreciate that the state of the art has evolved to a point where there is little difference between hardware, software, or a combination of hardware/software, the selection of hardware versus software to effectuate specific functions is a design choice left to an implementer. More specifically, one of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer.

In FIG. 4, the computing environment 220 comprises a computer 241, which typically includes a variety of computer readable media. Computer readable media can be any available media that can be accessed by computer 241 and includes both volatile and nonvolatile media, removable and non-removable media. The system memory 222 includes computer storage media in the form of volatile and/or nonvolatile memory such as read only memory (ROM) 223 and random access memory (RAM) 260. A basic input/output system 224 (BIOS), containing the basic routines that help to transfer information between elements within computer 241, such as during start-up, is typically stored in ROM 223. RAM 260 typically contains data and/or program modules that are immediately accessible to and/or presently being operated on by processing unit 259. By way of example, and not limitation, FIG. 4 illustrates operating system 225, application programs 226, other program modules 227, and program data 228.

The computer 241 may also include other removable/non-removable, volatile/nonvolatile computer storage media. By way of example only, FIG. 4 illustrates a hard disk drive 238 that reads from or writes to non-removable, nonvolatile magnetic media, a magnetic disk drive 239 that reads from or writes to a removable, nonvolatile magnetic disk 254, and an optical disk drive 240 that reads from or writes to a removable, nonvolatile optical disk 253 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 238 is typically connected to the system bus 221 through an non-removable memory interface such as interface 234, and magnetic disk drive 239 and optical disk drive 240 are typically connected to the system bus 221 by a removable memory interface, such as interface 235.

The drives and their associated computer storage media discussed above and illustrated in FIG. 4, provide storage of computer readable instructions, data structures, program modules and other data for the computer 241. In FIG. 4, for example, hard disk drive 238 is illustrated as storing operating system 258, application programs 257, other program modules 256, and program data 255. Note that these components can either be the same as or different from operating system 225, application programs 226, other program modules 227, and program data 228. Operating system 258, application programs 257, other program modules 256, and program data 255 are given different numbers here to illustrate that, at a minimum, they are different copies. A user may enter commands and information into the computer 241 through input devices such as a keyboard 251 and pointing device 252, commonly referred to as a mouse, trackball or touch pad. Other input devices (not shown) may include a microphone, joystick, game pad, satellite dish, scanner, or the like. These and other input devices are often connected to the processing unit 259 through a user input interface 236 that is coupled to the system bus, but may be connected by other interface and bus structures, such as a parallel port, game port or a universal serial bus (USB). The cameras 26, 28 and capture device 20 may define additional input devices for the console 100. A monitor 242 or other type of display device is also connected to the system bus 221 via an interface, such as a video interface 232. In addition to the monitor, computers may also include other peripheral output devices such as speakers 244 and printer 243, which may be connected through a output peripheral interface 233.

The computer 241 may operate in a networked environment using logical connections to one or more remote computers, such as a remote computer 246. The remote computer 246 may be a personal computer, a server, a router, a network PC, a peer device or other common network node, and typically includes many or all of the elements described above relative to the computer 241, although only a memory storage device 247 has been illustrated in FIG. 4. The logical connections depicted in FIG. 2 include a local area network (LAN) 245 and a wide area network (WAN) 249, but may also include other networks. Such networking environments are commonplace in offices, enterprise-wide computer networks, intranets and the Internet.

When used in a LAN networking environment, the computer 241 is connected to the LAN 245 through a network interface or adapter 237. When used in a WAN networking environment, the computer 241 typically includes a modem 250 or other means for establishing communications over the WAN 249, such as the Internet. The modem 250, which may be internal or external, may be connected to the system bus 221 via the user input interface 236, or other appropriate mechanism. In a networked environment, program modules depicted relative to the computer 241, or portions thereof, may be stored in the remote memory storage device. By way of example, and not limitation, FIG. 4 illustrates remote application programs 248 as residing on memory device 247. It will be appreciated that the network connections shown are exemplary and other means of establishing a communications link between the computers may be used.

The computer readable storage media described above may have stored thereon instructions for scanning a human in a captured scene. The computer executable instructions may comprise instructions for receiving a depth image of a physical space, wherein the depth image includes data representative of a gesture, and rendering visual assistance representing instructional gesture data for the gesture. The computer readable storage media described above may have stored thereon instructions for determining whether to provide instructional data. The instructions may comprise receiving image data for a scene, wherein the image data includes data representative of a gesture, comparing the data representative of the gesture to at least one output of a gesture filter, detecting a variation between the data representative of the gesture and the at least one output of the gesture filter, wherein the variation is indicative of a failure in an execution of the gesture; and based on the variation, determining whether to provide instructional gesture data.

Figure 5A:
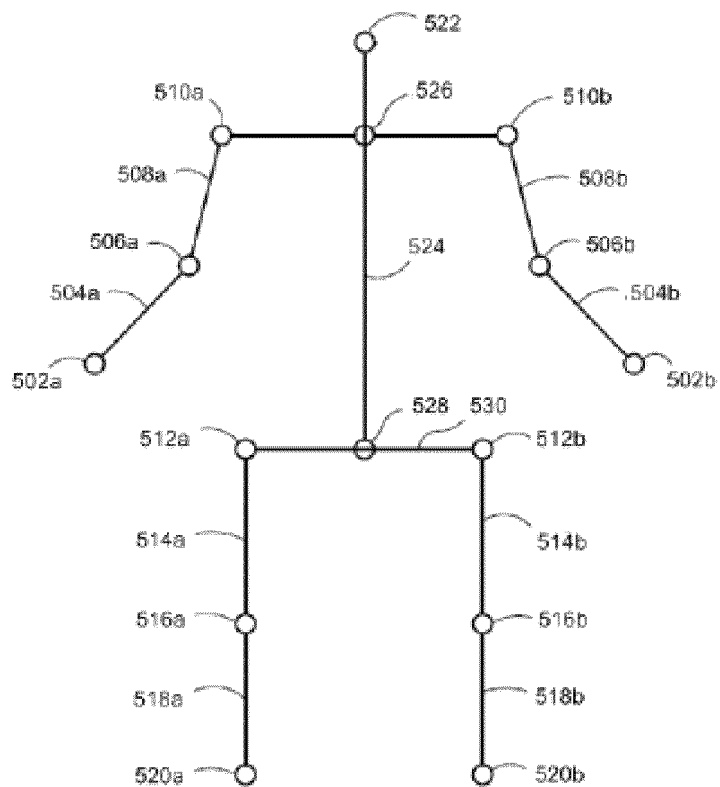
FIG. 5A illustrates a skeletal mapping of a user that has been generated from a depth image.

FIG. 5A depicts an example skeletal mapping of a user that may be generated from the capture device 20. In this embodiment, a variety of joints and bones are identified: each hand 502, each forearm 504, each elbow 506, each bicep 508, each shoulder 510, each hip 512, each thigh 514, each knee 516, each foreleg 518, each foot 520, the head 522, the torso 524, the top 526 and bottom 528 of the spine, and the waist 530. Where more points are tracked, additional features may be identified, such as the bones and joints of the fingers or toes, or individual features of the face, such as the nose and eyes.

Through moving his body, a user may create gestures. A gesture comprises a motion or pose by a user that may be captured as image data and parsed for meaning A gesture may be dynamic, comprising a motion, such as mimicking throwing a ball. A gesture may be a static pose, such as holding one's crossed forearms 504 in front of his torso 524. A gesture may be a single movement (e.g., a jump) or a continuous gesture (e.g., driving), and may be short in duration or long in duration (e.g., driving for 20 minutes). A gesture may also incorporate props, such as by swinging a mock sword. A gesture may comprise more than one body part, such as clapping the hands 502 together, or a subtler motion, such as pursing one's lips.

A user's gestures may be used for input in a general computing context. For instance, various motions of the hands 502 or other body parts may correspond to common system wide tasks such as navigate up or down in a hierarchical list, open a file, close a file, and save a file. For instance, a user may hold his hand with the fingers pointing up and the palm facing the capture device 20. He may then close his fingers towards the palm to make a fist, and this could be a gesture that indicates that the focused window in a window-based user-interface computing environment should be closed. Gestures may also be used in a video-game-specific context, depending on the game. For instance, with a driving game, various motions of the hands 502 and feet 520 may correspond to steering a vehicle in a direction, shifting gears, accelerating, and breaking Thus, a gesture may indicate a wide variety of motions that map to a displayed user representation, and in a wide variety of applications, such as video games, text editors, word processing, data management, etc.

A user may generate a gesture that corresponds to walking or running, by walking or running in place himself. For example, the user may alternately lift and drop each leg 512-520 to mimic walking without moving. The system may parse this gesture by analyzing each hip 512 and each thigh 514. A step may be recognized when one hip-thigh angle (as measured relative to a vertical line, wherein a standing leg has a hip-thigh angle of 0°, and a forward horizontally extended leg has a hip-thigh angle of 90°) exceeds a certain threshold relative to the other thigh. A walk or run may be recognized after some number of consecutive steps by alternating legs.

The time between the two most recent steps may be thought of as a period. After some number of periods where that threshold angle is not met, the system may determine that the walk or running gesture has ceased.

Given a "walk or run" gesture, an application may set values for parameters associated with this gesture. These parameters may include the above threshold angle, the number of steps required to initiate a walk or run gesture, a number of periods where no step occurs to end the gesture, and a threshold period that determines whether the gesture is a walk or a run. A fast period may correspond to a run, as the user will be moving his legs quickly, and a slower period may correspond to a walk.

A gesture may be associated with a set of default parameters at first that the application may override with its own parameters. In this scenario, an application is not forced to provide parameters, but may instead use a set of default parameters that allow the gesture to be recognized in the absence of application-defined parameters. Information related to the gesture may be stored for purposes of pre-canned gesture animation.

There are a variety of outputs that may be associated with the gesture. There may be a baseline "yes or no" as to whether a gesture is occurring. There also may be a confidence level, which corresponds to the likelihood that the user's tracked movement corresponds to the gesture. This could be a linear scale that ranges over floating point numbers between 0 and 1, inclusive. Wherein an application receiving this gesture information cannot accept false-positives as input, it may use only those recognized gestures that have a high confidence level, such as at least 0.95. Where an application must recognize every instance of the gesture, even at the cost of false-positives, it may use gestures that have at least a much lower confidence level, such as those merely greater than 0.2. The gesture may have an output for the time between the two most recent steps, and where only a first step has been registered, this may be set to a reserved value, such as −1 (since the time between any two steps must be positive). The gesture may also have an output for the highest thigh angle reached during the most recent step.

Another exemplary gesture is a "heel lift jump." In this, a user may create the gesture by raising his heels off the ground, but keeping his toes planted. Alternatively, the user may jump into the air where his feet 520 leave the ground entirely. The system may parse the skeleton for this gesture by analyzing the angle relation of the shoulders 510, hips 512 and knees 516 to see if they are in a position of alignment equal to standing up straight. Then these points and upper 526 and lower 528 spine points may be monitored for any upward acceleration. A sufficient combination of acceleration may trigger a jump gesture. A sufficient combination of acceleration with a particular gesture may satisfy the parameters of a transition point.

Given this "heel lift jump" gesture, an application may set values for parameters associated with this gesture. The parameters may include the above acceleration threshold, which determines how fast some combination of the user's shoulders 510, hips 512 and knees 516 must move upward to trigger the gesture, as well as a maximum angle of alignment between the shoulders 510, hips 512 and knees 516 at which a jump may still be triggered. The outputs may comprise a confidence level, as well as the user's body angle at the time of the jump.

Setting parameters for a gesture based on the particulars of the application that will receive the gesture is important in accurately identifying gestures. Properly identifying gestures and the intent of a user greatly helps in creating a positive user experience.

An application may set values for parameters associated with various transition points to identify the points at which to use pre-canned animations. Transition points may be defined by various parameters, such as the identification of a particular gesture, a velocity, an angle of a target or object, or any combination thereof If a transition point is defined at least in part by the identification of a particular gesture, then properly identifying gestures assists to increase the confidence level that the parameters of a transition point have been met.

Another parameter to a gesture may be a distance moved. Where a user's gestures control the actions of an avatar in a virtual environment, that avatar may be arm's length from a ball. If the user wishes to interact with the ball and grab it, this may require the user to extend his arm 502-510 to full length while making the grab gesture. In this situation, a similar grab gesture where the user only partially extends his arm 502-510 may not achieve the result of interacting with the ball. Likewise, a parameter of a transition point could be the identification of the grab gesture, where if the user only partially extends his arm 502-510, thereby not achieving the result of interacting with the ball, the user's gesture also will not meet the parameters of the transition point.

A gesture or a portion thereof may have as a parameter a volume of space in which it must occur. This volume of space may typically be expressed in relation to the body where a gesture comprises body movement. For instance, a football throwing gesture for a right-handed user may be recognized only in the volume of space no lower than the right shoulder 510$a$, and on the same side of the head 522 as the throwing arm 502$a$-310$a$. It may not be necessary to define all bounds of a volume, such as with this throwing gesture, where an outer bound away from the body is left undefined, and the volume extends out indefinitely, or to the edge of scene that is being monitored.

Figure 5B:
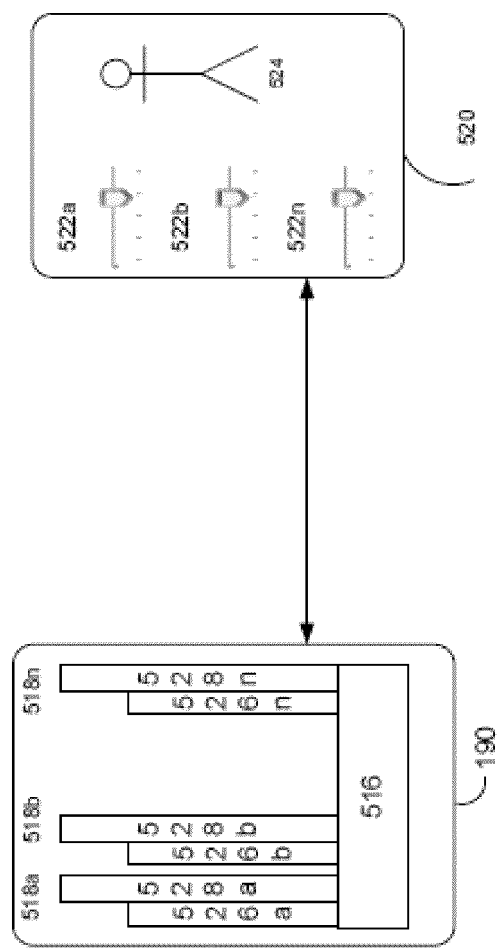
FIG. 5B illustrates further details of the gesture recognizer architecture shown in FIG. 2.

FIG. 5B provides further details of one exemplary embodiment of the gesture recognizer engine 190 of FIG. 2. As shown, the gesture recognizer engine 190 may comprise at least one filter 518 to determine a gesture or gestures. A filter 518 comprises information defining a gesture 526 (hereinafter referred to as a "gesture"), and may comprise at least one parameter 528, or metadata, for that gesture. For instance, a throw, which comprises motion of one of the hands from behind the rear of the body to past the front of the body, may be implemented as a gesture 526 comprising information representing the movement of one of the hands of the user from behind the rear of the body to past the front of the body, as that movement would be captured by the depth camera. Parameters 528 may then be set for that gesture 526. Where the gesture 526 is a throw, a parameter 528 may be a threshold velocity that the hand has to reach, a distance the hand must travel (either absolute, or relative to the size of the user as a whole), and a confidence rating by the recognizer engine that the gesture occurred. These parameters 528 for the gesture 526 may vary between applications, between contexts of a single application, or within one context of one application over time.

Filters may be modular or interchangeable. In an embodiment, a filter has a number of inputs, each of those inputs having a type, and a number of outputs, each of those outputs having a type. In this situation, a first filter may be replaced with a second filter that has the same number and types of inputs and outputs as the first filter without altering any other aspect of the recognizer engine architecture. For instance, there may be a first filter for driving that takes as input skeletal data and outputs a confidence that the gesture associated with the filter is occurring and an angle of steering. Where one wishes to substitute this first driving filter with a second driving filter—perhaps because the second driving filter is more efficient and requires fewer processing resources—one may do so by simply replacing the first filter with the second filter so long as the second filter has those same inputs and outputs—one input of skeletal data type, and two outputs of confidence type and angle type.

A filter need not have a parameter. For instance, a "user height" filter that returns the user's height may not allow for any parameters that may be tuned. An alternate "user height" filter may have tunable parameters—such as to whether to account for a user's footwear, hairstyle, headwear and posture in determining the user's height.

Inputs to a filter may comprise things such as joint data about a user's joint position, like angles formed by the bones that meet at the joint, RGB color data from the scene, and the rate of change of an aspect of the user. Outputs from a filter may comprise things such as the confidence that a given gesture is being made, the speed at which a gesture motion is made, and a time at which a gesture motion is made.

A context may be a cultural context, and it may be an environmental context. A cultural context refers to the culture of a user using a system. Different cultures may use similar gestures to impart markedly different meanings. For instance, an American user who wishes to tell another user to "look" or "use his eyes" may put his index finger on his head close to the distal side of his eye. However, to an Italian user, this gesture may be interpreted as a reference to the mafia.

Similarly, there may be different contexts among different environments of a single application. Take a first-person shooter game that involves operating a motor vehicle. While the user is on foot, making a first with the fingers towards the ground and extending the first in front and away from the body may represent a punching gesture. While the user is in the driving context, that same motion may represent a "gear shifting" gesture. There may also be one or more menu environments, where the user can save his game, select among his character's equipment or perform similar actions that do not comprise direct game-play. In that environment, this same gesture may have a third meaning, such as to select something or to advance to another screen.

Filters can be run side by side, and multiple filters may look for the same things but different execution. Thus, the number of filters may increased depending on the permutation of motion that could define a gesture. For example, a curve ball may be an overhand gesture, but then, a player may prefer to throw underhand if they are successful that way.

The gesture recognizer engine 190 may have a base recognizer engine 516 that provides functionality to a gesture filter 518. In an embodiment, the functionality that the recognizer engine 516 implements includes an input-over-time archive that tracks recognized gestures and other input, a Hidden Markov Model implementation (where the modeled system is assumed to be a Markov process—one where a present state encapsulates any past state information necessary to determine a future state, so no other past state information must be maintained for this purpose—with unknown parameters, and hidden parameters are determined from the observable data), as well as other functionality required to solve particular instances of gesture recognition.

Filters 518 are loaded and implemented on top of the base recognizer engine 516 and can utilize services provided by the engine 516 to all filters 518. In an embodiment, the base recognizer engine 516 processes received data to determine whether it meets the requirements of any filter 518. Since these provided services, such as parsing the input, are provided once by the base recognizer engine 516 rather than by each filter 518, such a service need only be processed once in a period of time as opposed to once per filter 518 for that period, so the processing required to determine gestures is reduced.

An application may use the filters 518 provided by the recognizer engine 190, or it may provide its own filter 518, which plugs in to the base recognizer engine 516. In an embodiment, all filters 518 have a common interface to enable this plug-in characteristic. Further, all filters 518 may utilize parameters 528, so a single gesture tool as described below may be used to debug and tune the entire filter system 518.

These parameters 528 may be tuned for an application or a context of an application by a gesture tool 520. In an embodiment, the gesture tool 520 comprises a plurality of sliders 522, each slider 522 corresponding to a parameter 528, as well as a pictoral representation of a body 524. As a parameter 528 is adjusted with a corresponding slider 522, the body 524 may demonstrate both actions that would be recognized as the gesture with those parameters 528 and actions that would not be recognized as the gesture with those parameters 528, identified as such. This visualization of the parameters 528 of gestures provides an effective means to both debug and fine tune a gesture.

Figure 6A:
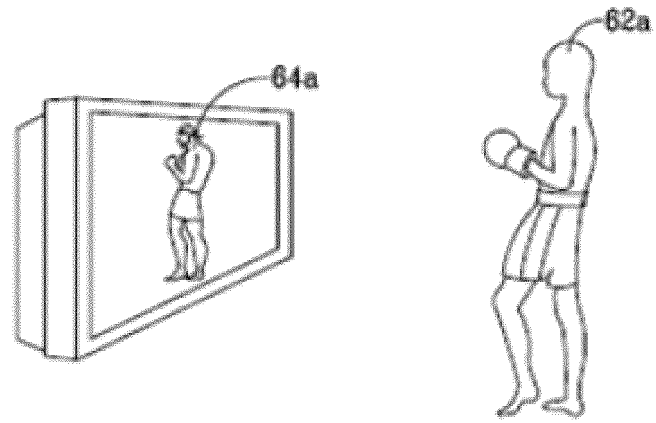
FIGS. 6A-6D illustrate another example embodiment of target recognition, analysis and tracking with a user playing a boxing game.
Figure 6B:
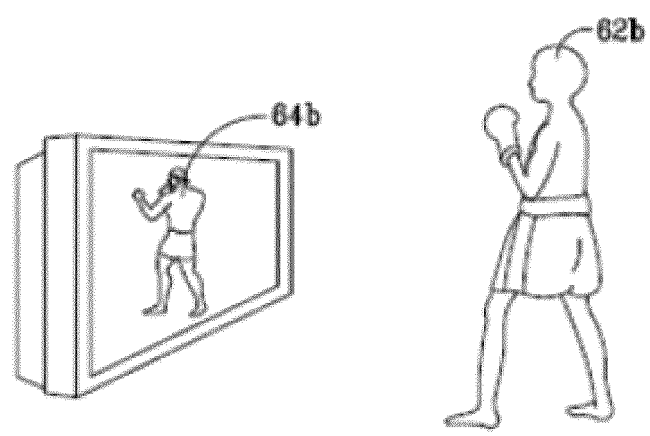
Figure 6C:
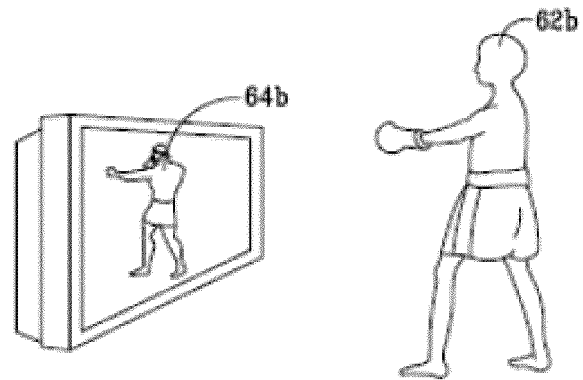

The example of an application executing on the computing environment shown in FIGS. 6A-6C is a boxing game that a user may be playing. FIGS. 6A-6C represent a user's punching gesture in the physical space, 62a, 62b, 62c, where the visual representation of the user, 64a, 64b, 64c maps to the user's motions in the physical space. Each of FIGS. 6A-6C illustrate the user's position in the physical space at three discrete points of time during the user's punching gesture, 62a, 62b, 62c and an example of the visual representation of the user, 64a, 64b, 64c, displayed in the application space. The rate that frames of image data are captured and displayed determines the level of continuity of the displayed motion of the visual representation. Though additional frames of image data may be captured and displayed, the frames depicted in FIGS. 6A-6C are selected for exemplary purposes.

Figure 6D:
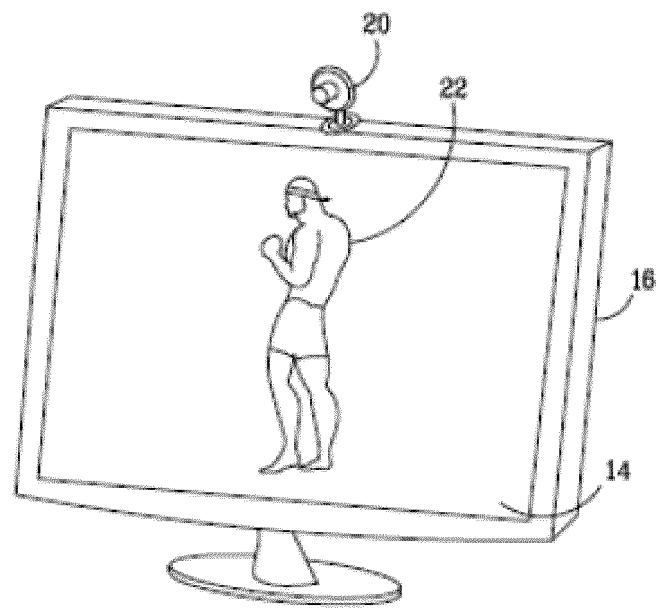

The capture device 20 may capture, analyze, and track the user's motions made in the physical space, such as the user's punching gesture 62a, 62b, 62c. According to an example embodiment, the capture device 20 may be configured to capture video with depth information including a depth image of a scene. The capture device 20 may provide the depth information and images captured and a skeletal model that may be generated by the capture device 20 for display by the audiovisual component 16. The user may view the image or visual representation of the user, 64a, on an audiovisual device 16, such as a television screen shown in FIG. 6D.

The audiovisual device 16 may provide a visual representation of a player avatar, 64a, 64b, 64c, that the user may control with his or her movements. The user's motions may map to the visual representation in the application space to perform one or more controls or actions within the application. For example, the user may be tracked using the capture device 20 such that gestures of user 18 may be interpreted as controls that may affect the application being executed by the computer environment. In the boxing game application, the user's gesture in the physical space in the form of a punching motion, 62a, 62b, 62c, controls the gestures made by the visual representation, 64a, 64b, 64c, causing a punch to occur in the game space. Thus, according to an example embodiment, a computer environment and the capture device 20 of the target recognition, analysis, and tracking system 10 may be used to recognize and analyze the punch of the user 18 in physical space such that the punch may be interpreted as a game control of the player avatar 40 in the game space. The visual representation may be mapped to the user's gestures and displayed in real-time with respect to the execution of the gesture in the physical space.

It may be desirable in some situations to provide visual assistance representing instructional gesture data to teach a user how to gesture properly. Instructional gesture data can teach a user how to gesture properly to control the executing application. In an example embodiment, the computing system or the executing application may identify errors in a user's gesture and provide instructional gesture data to highlight the errors. In another example embodiment, the user selects a training session or enters into training mode to learn how to gesture properly.

Figure 7A:
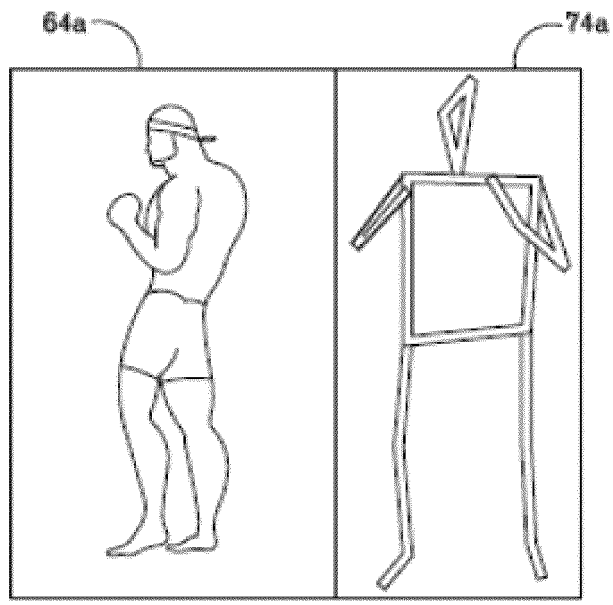
FIGS. 7A-7D illustrate an example display of visual assistance side-by-side with a visual representation of a user's gestures.
Figure 7B:
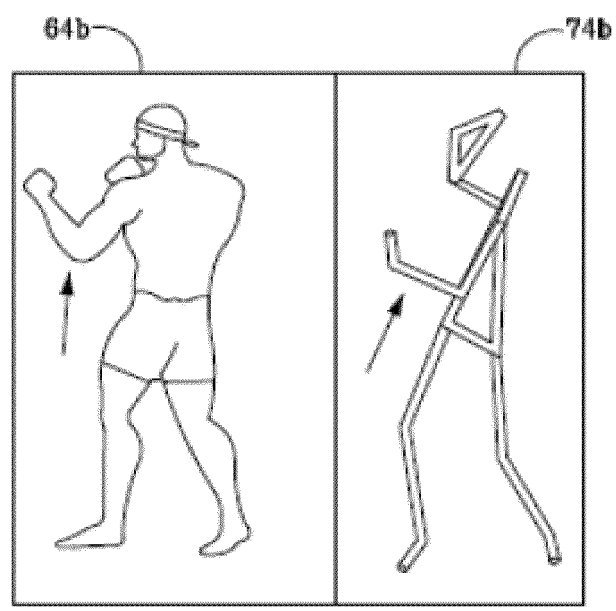
Figure 7C:
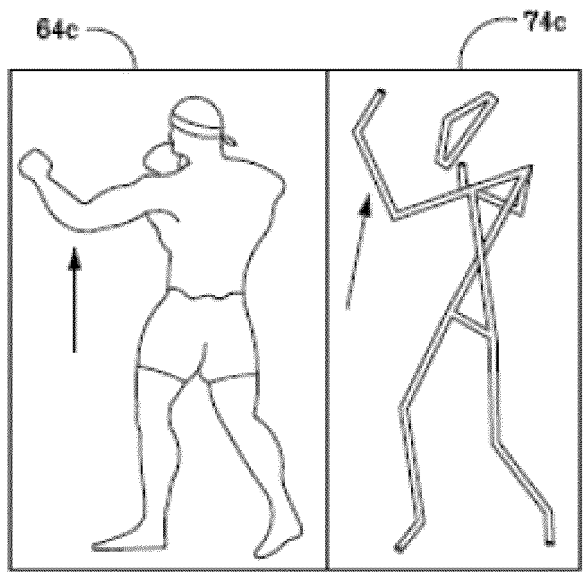
Figure 7D:
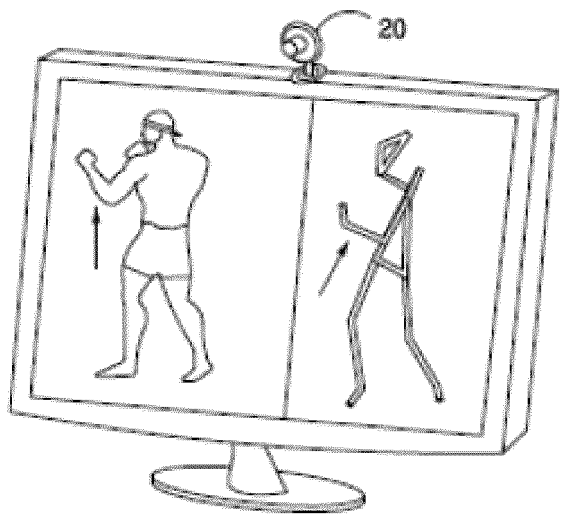

FIGS. 7A-C depict example split-screen screenshots for replaying a user's gestures as an avatar, with instructional gesture data displayed side-by-side with the avatar. The left side of each split-screen renders the visual representation of a user's gestures at the three discrete points of time during the user's punching gesture, 64*a*, 64*b*, 64*c*, as shown in FIGS. 6A-6C. The right side of each split-screen renders an example embodiment of visual assistance representing instructional gesture data, 74*a*, 74*b*, 74*c*, corresponding to each of the frames of image data 64*a*, 64*b*, 64*c*. FIG. 7D depicts the display portion of system 10 from FIGS. 1A and 1B, showing an example embodiment for displaying the split screen. In this example, the left side of each of FIGS. 7A-7C corresponds to a snapshot or frame of image data as captured by a depth camera, a parallel RGB camera, or images combined from both cameras. On the right side of the split-screen, the system displays visual assistance that highlights an error in the user's gesture.

The visual assistance can be a demonstration of proper motion. For example, the user could select a training session for punches and the system could initiate an interactive training session that teaches the user the motion for a particular punch. The system can display the user's motion, live or replayed, along with the visual assistance, highlighting any errors in the user's motion. Various display techniques to highlight the errors in the user's gestures. The assistance can portray the delta between the user's actual position and the ideal position. For example, the arrows in FIGS. 7B and 7C point to a part of the avatar's body, 64*a*, 64*b*, 64*c*, that represents the user's positioning in the physical space, exemplifying how the user's positioning varies from an ideal gesture position at that point in time, 74*a*, 74*b*, 74*c*.

The system may provide visual assistance for training purposes to demonstrate the appropriate motions to control the system or an executing application. The training may be part of a training mode that the user actively selects to enter. The user may also request training, such as the first time the user executes an application. Various events may trigger the display of visual assistance for gesture demonstration. The system may detect an error in the user's motion or a deviation from an expected motion. The system may identify areas of a user's positioning throughout the gesture that could be improved to achieve higher success in the executing application. A user's gesture may not be one that corresponds to a recognized gesture, indicating that the user is unfamiliar with the applicable gestures. The system may predict the user's intended gesture and provide an option for training the user to properly make that gesture. The system may recognize an inexperienced user and offer training Any of these events may trigger the display of visual assistance comprising instructional gesture data.

The system or application may comprise a training mode and an execution mode. The training mode may be entered into automatically as a result of a trigger, such as those described above. For example, if the user 18 is throwing a punch in the physical space that does not correspond to a recognized gesture, the system 10 may interrupt the application, enter into a training mode, and provide visual assistance that demonstrates appropriate gestures to the user.

The system may identify an error in the user's motion by evaluating the user's position in a single frame of captured data or over a series of frames. For example, the system may recognize a user's gesture as an uppercut punching motion, identified by movement within certain volumes of space with respect to the user. The system may also identify that, in certain frames of image data, the user is not moving his arm properly in the physical space or that changes in the user's motion could give more success in the boxing game.

The system may identify errors based on the certain parameters of the user's measured gesture, such as a deviation from an ideal velocity range or if the user's measured gesture falls outside the expected volumes of space. For example, a baseball application may direct the user to make an overhand throwing motion to throw a ball to a batter. A depth camera or an RGB camera may identify aspects of the user's motions in the physical space, and a gesture filter 191 may identify the motion to be in a class of throwing gestures. The parameters for various classes of throwing gestures may be distinguished based on the volume of space monitored around a user's head. An overhand throw may be the volume of space in front and behind the user's head but above the user's throwing shoulder. An underhand throw may be defined by a volume of space in front and below a user's waist, the volume extending between the shoulder and the user's waist. The gesture filter may identify an overhand throw based on parameters of the user's motion in the physical space. The gesture filter may expect an overhand throw (or an attempted overhand throw) due to the point of execution in the application (e.g., the user is at a point in a baseball application where the user is directed to throw a ball to a batter). Deviations from the filter parameters or the failure to meet threshold levels of acceptance may trigger the display of visual assistance.

The display of the visual assistance comprising instructional gesture data can take any suitable form. The instructional gesture data, 74*a*, 74*b*, 74*c*, in this embodiment, is displayed as a stick figure representation, but it is contemplated that the visual representation may take on any suitable representation. For example, arrows or highlighted sections of the visual representation of the user may indicate proper gesturing, as shown in FIGS. 7A-7D. The display could be side-by-side representations of the user's gesture and the ideal gesture, also shown in FIGS. 7A-7D. The visual assistance could be in the form of replayed motion (at the rate of capture, slowed, fast, etc) or displayed in real-time. As shown in FIG. 8A, an image representing the instructional gesture data could be ghosted or superimposed over the visual representation.

The left side of each of FIGS. 7A-7C may correspond directly to a snapshot or frame of image data as captured by a depth camera and/or an RGB camera. The selected frames of image data may be replayed at any speed and can be viewed in a continuous replay of motion or one at a time as separate screen captures. The frames of image data may be replayed at a speed that corresponds to frames per second rate of capture. Instructional gesture data, such as that shown on the right hand side of each of FIGS. 7A-7C, may correspond to the frames of image data shown on the left side. Any number of frames of image data may be captured and any number of corresponding frames of instructional gesture data may be generated for any given gesture. Thus, additional frames of image data and corresponding instructional gesture data may be available. The user can pause, scroll, view, zoom, etc the display of visual assistance.

The screenshot of image data on the left side of FIG. 7B depicts the user's gesture 64b at a second point in time. On the right side of the split-screen, the system displays visual assistance that highlights an error in the user's gesture. Displaying the visual representation of the user's gesture side by side with instructional gesture data that highlights an error in the user's gesture may assist the user to correct his or her motion in the physical space. For example, FIG. 7B highlights the error in the user's gesture by pointing with an arrow to the position of the user's arm. In this example, the visual assistance points to a better position for the user's arm at that point in the gesture to teach the user how to properly make an uppercut motion or to be more successful in the boxing game. Similarly, FIG. 7C depicts a screenshot of the user's image data, pointing out that at that point in the uppercut punching gesture, the user will achieve better success if he or she completes the motion with his arm in a higher position. The side by side depiction can demonstrate the delta between the user's actual position and the ideal position.

The system can display the user's motion along with live or real-time visual assistance to highlight the errors in the user's motion. Thus, instead of the screenshots of image data in FIGS. 7A-7C being a replay of the user's gesture, the user may gesture in the physical space and view live visual assistance on the right side of each split-screen. For example, the instructional gesture data may be provided in an interactive training session. The training session may demonstrate the proper positioning at discrete points in time throughout the uppercut punching gesture. At each discrete point, the user can gesture in the physical space and observe, in real time, the user's gesture as it compares to the visual assistance showing the proper gesture position. The user can cycle through various points in time, learning and performing the proper gesture at each point and receiving real-time visual assistance regarding the ideal position that the user should be in at that time. The user can correct his or her motion frame by frame.

While FIGS. 7A-7C depict a split-screen display of the visual representation of the user and the instructional gesture data, it is contemplated that the instructional gesture data may be provided in any suitable form. For example, rather than a split screen, just the left side of the split-screen in FIGS. 7A-7C may be displayed to highlight the errors in the user's gesture. The errors are highlighted, in this example, as arrows that point to the deviation of the user's gesture. In another example, or combined with another form of instructional gesture data, auditory assistance such as a voice-over could verbalize the errors or possible corrections for the user.

The instructional gesture data may indicate a proper alignment of the user in the physical space to inform the user how to move into proper view of the capture device's field of capture. For example, if a particular gesture filter is failing to provide a confident result for a gesture because the motion of a limb captured by the capture device is moving out of view of the capture device's field of capture, the instructional gesture data may comprise a set of training data or assistance that informs the user that they need to move in the physical space for better alignment with the capture device. For example, a voice-over may say "please step to your left," or the visual representation of the user on the screen, such as that shown by 64a, 64b, and 64c, may only show a portion of the visual representation on the screen, indicating that the user needs to realign himself or herself in the physical space.

FIGS. 8A and 8B depict additional examples of providing instructional gesture data to a user. In FIG. 8A, a representation of a corrected gesture animation, shown as a stick figure representation, is superimposed or overlaid over the user's visual representation. Thus, an indication of proper motion overlaps the user's image data. The user can replay his or her motion and view the instructional gesture data that overlaps the visual representation of the user's gesture. The user can then observe the delta between the user's actual position and the ideal position. An arrow is just one example for providing a visual representation of the delta between the user's arm position and the visual assistance. Highlighting the delta allows the user to determine what modifications could improve the gesture in the physical space.

The training data may be displayed as an overlay, as shown in FIG. 8A, during the execution of the application, such as a game that is in progress. Thus, it may not be necessary to interrupt the game to go into a separate training mode. Instructional gesture data may comprise hints or small suggestions to the user's motion, and the hints may be expressed as an overlay in the game such that the game play continues uninterrupted while providing the instructional gesture data.

The example display of visual assistance in FIG. 8B is a visual representation of the instructional gesture data that includes a demonstration of the gesture. The demonstration may be broken up into phases or be a continuous video clip. The visual representation of the instructional gesture data may be in any suitable form, such as in the form of a skeletal representation, a ghosted image, or a player avatar.

The application may trigger entry into a training mode as a result of a selection of a training mode by the user, a detection of user gesture error, the initiation of an application, or the like. For example, upon detection of an error in the user's gesture, an optional entry into training mode may be offered to the user. The system may not recognize the gesture made by the user and offer suggestions for training based on predictions of the user's intended motion. The system may recognize the gesture and offer suggestions as to a better gesture applicable to the application at that point in time, or offer suggestions for training to better gesture the gesture made by the user for more success in the application.

FIG. 9 depicts an example of options, 902a, 902b, 902c, 902d, that the system may display to a user in a boxing game. The display device 16 can display options for the predicted gesture(s), and the user can select an option to receive training to properly perform or improve performance of the gesture. The possible gestures may be any gesture applicable to a gesture-based system, an executing application, a plug-in with supplemental gestures, or the like. The options shown in FIG. 9, 902a, 902b, 902c, 902d, are applicable to the executing application, a boxing game.

In this example, the user's gesture in the physical space is identified as a punching gesture. As described above, a gestures recognition engine 190 may include a collection of gesture filters 191. Each filter 191 may comprise information defining a gesture along with parameters, or metadata, for that gesture. The data captured by the cameras 26, 28 and device 20 in the form of the skeletal model and movements associated with it may be compared to the gesture filters in the gesture library 190 to identify when a user has performed one or more gestures.

In an example embodiment, the system gathers and stores history data for a particular user, such as storing history data in a user profile. The system could adapt the filter parameters and the threshold level for the user based on this history data. For example, the filter parameters for the volume of space that are used to identify the gesture as an overhand throw may be set to default values in accordance with research or simulation data. A user's hand, however, may tend to be a distance further from the user's head than is common, and therefore outside the bounds of the volume of space set for an overhand throw. Initially, the variation may be indicative of a failure in the execution of the gesture, triggering a display or options for entering a training mode to learn how to execute the gesture. Over time, the system may gather data with respect to the user and modify the filter parameters to accommodate for the user's tendencies. For example, the parameters that define volume of space could be modified to shift the volume of space to more closely align with the user's body position. A threshold level of acceptance could also vary accordingly The training session may be interactive such that the user's actual motion is evaluated, highlighted, corrected, etc, such as in the manner described in FIGS. 7A-7C. The visual assistance may be a demonstration of proper gestures applicable to an application that a user can practice in the physical space without a visual representation of the user's motion. FIG. 8B depicts an example of the demonstration of a proper gesture via separate frames of motion. The demonstration may highlight positions that the user's should place his or her body to properly perform the gesture. The demonstration may be irrespective of the user's gestures. Alternately, the visual assistance may be a result of an evaluation of the user's gestures, where the visual assistance pinpoints specific areas for improvement specific to the user.

Other techniques for displaying the visual assistance are possible. For example, a visual representation of the instructional gesture data may be on a portion of the display space, wherein the portion is smaller than a total display space. The visual assistance providing instructional gesture data may comprise a coach, such as a user-created coach, a human coach, a prerecorded coach, or the like. The coach may pop-up as a video feed. The coach may provide verbal instructions that correspond to the demonstrated gesture. A user could learn a gesture, such as how to throw a baseball, by accessing a training program. From the basics, the coach could walk the user through the gestures that make up a throw. The user may select a specific coach, such as from a collection of avatars that represent real or invented personas. Different personalities could be used, such as a famous baseball player. The representation of the coach may be prerecorded data displayed along with a demonstrated gesture. Alternately, the visual assistance may be a human coach, displayed live in real-time from another user. The visual assistance may be in the form of a voice-over or a live coach that provides gesture demonstration via a network.

FIG. 10 depicts an example of two users remotely connected and interacting through a boxing game application. The remote connection may be over a network, for example. The network may be managed by a host and may be a subscription-based system. Such a connection enables users to be remotely connected or networked such that multiple users can interact via their respective computing environments.

For example, consider first and second remote users executing a gaming application, playing as a team over a remote connection against other users. The first user may recognize that the second user is performing a certain motion incorrectly and is therefore causing failure in the game for the team. The first user may provide, in real-time, the demonstration of a gesture, 1002*a*, such that the second user can observe the visual assistance on the display in the second user's computing environment, 1002*b*. The second user's computing environment may receive information related to the demonstrated gesture and provide visual assistance to the second user. The visual assistance may be provided live to the second user, delayed only by the time it takes to transmit from the first user, and process and display the information to the second user. Suitable technology can be implemented such that transmission and processing times are fast, minimizing the delay of visual assistance to the second user based on the first user's live gesture demonstration.

The display of a visual representation of user #1 to user #2 in real-time may be a result of numerous triggers. For example, user #1 may request instruction from user #2, user #2 may recognize errors in user #1's gestures, users may interact for the purpose of learning tactics from each other, etc. The users may pause the application and have an interactive training session. User #1's computing environment may display a visual representation of user #2, simulating an in-person training session. User #2 can communicate, display motion, etc, that is simulated to user #2.

Figure 11A:
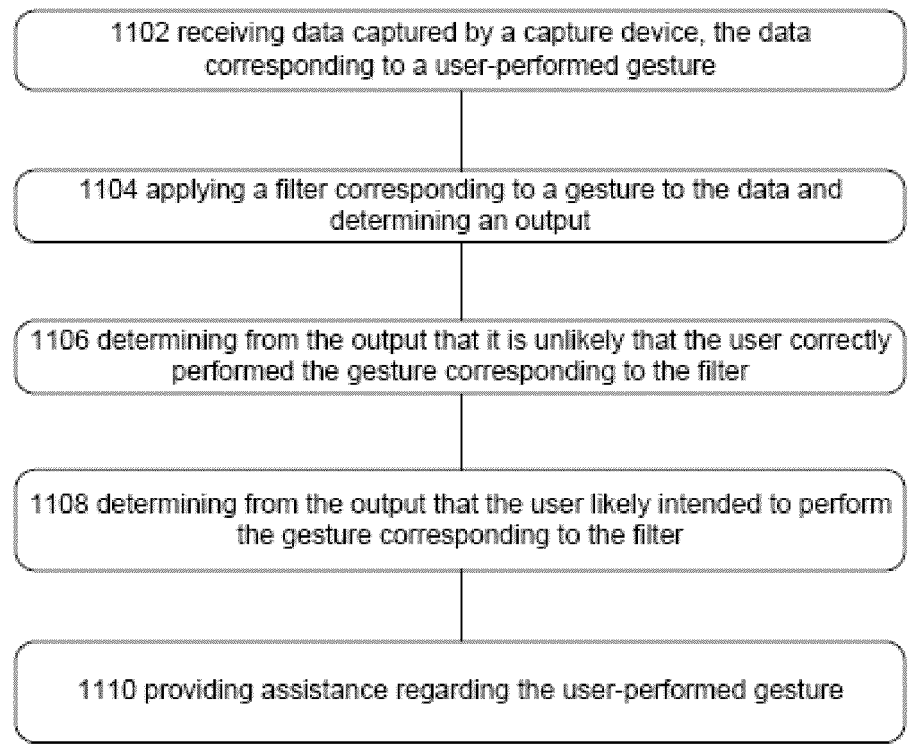
FIG. 11A depicts example operating procedures for gesture coaching.

FIG. 11A depicts exemplary operational procedures for a gesture coach.

Operation 1102 depicts receiving data captured by a capture device 20, the data corresponding to a user-performed gesture. The capture device may capture a scene that contains all of the user, such as from the floor to the ceiling and to the wall on each side of a room at the distance in which the user is located. The capture device may also capture a scene that contains only part of the user, such as the user from the abdomen up as he or she sits at a desk. The capture device may also capture an object controlled by the user, such as a prop camera that the user holds in his or her hand.

Operation 1104 depicts analyzing the data to produce an output corresponding to whether the data corresponds to a system-recognized gesture. In an embodiment, this analyzing may be performed with a filter 518 applied to the data by gesture recognizer engine 190.

Operation 1106 depicts determining from the output that it is unlikely that the user correctly performed the system-recognized gesture. In an embodiment, the system-recognized gesture comprises a gesture corresponding to the filter.

In an embodiment, the output comprises a confidence level. In an embodiment, is unlikely that the user correctly performed the gesture corresponding to the filter when the confidence level is below a threshold. That threshold may be the level at which it is likely that the user correctly performed the gesture. There may be a difference between the threshold level above which it is likely that the user correctly performed the gesture and the threshold level below which it is unlikely that the user performed the gesture, with levels between those two thresholds being neither considered likely nor unlikely.

In an embodiment where the gesture filter comprises multiple outputs, it may be unlikely that the user correctly performed the gesture when at least one output corresponds to it being unlikely that the user correctly performed the gesture. For instance, a "automobile steering" filter may comprise outputs for the distance between the user's hands, the position of the user's hands relative to the rest of his body, and an angle at which the hands are tilted. It may be likely that the user is performing the steering gesture where he has his hands 12-18" apart, in front of his chest, and each hand displays a rotational angle off vertical that corresponds to the same steering angle. Where the user correctly spaces his hands and places them in front of his chest, yet rotates both hands outward, such that his left hand signifies steering to the left and his right hand signifies steering to the right, that only one of these parameters is not met may be sufficient to determine that it is unlikely that the user correctly performed the gesture.

Operation 1108 determining from the output that the user likely intended to perform the system-recognized gesture.

In an embodiment where a user must sustain a gesture, such as by holding the steering position for a prolonged period of time while the user steers, it may be determined that the user likely intended to perform the gesture where an output at least occasionally corresponds to that gesture being performed, but does not correspond to that gesture being performed for an extended period of time.

In an embodiment where the gesture filter comprises multiple outputs, it may be likely that the user intended to perform the gesture when at output corresponds to the user performing the gesture. For instance, given the "automobile steering" filter discussed above, it may be that the user has correct hand spacing, and his respective hand rotation angles correspond to the same steering direction, but instead of holding his hands in front of his body, he has them at a nearly relaxed position by his sides. In this instance, where two of the outputs (hand spacing and hand rotation angles) show that it is likely that the user intended to make the steering gesture, but a third output (hand position) does not, it may be determined that the user intended to perform the gesture.

Operation 1110 depicts providing assistance regarding the user-performed gesture.

In an embodiment, providing assistance comprises adjusting the output, and sending the adjusted output to an application corresponding to the user-performed gesture. This may be akin to relaxing the parameters or tolerance of an application. Where it is determined that the user intended to perform the gesture, the outputs for the corresponding gesture filter may be changed to be outputs that correspond to the gesture likely being performed, while still maintaining the user's intent. For instance, where the user appears to intend to steer a vehicle sharply to the left, but has incorrect hand position, the outputs corresponding to hand position may be adjusted, while still corresponding to the vehicle steering sharply to the left (as opposed to a turn to the soft left, or a turn to the right).

In an embodiment, adjusting the output comprises increasing a responsiveness of the filter. For instance, the user may make small movements that likely correspond to the user intending, but failing, to perform a gesture. With a steering gesture, this could comprise rotating his hands only a small amount when he wants to turn, no matter how sharply. These movements may be amplified. Where the user rotates his hands a maximum of 20°, and a rotation of 90° corresponds to the sharpest turn, the user's actual rotation may be multiplied by a factor of 4.5, such that his 20° rotation is treated as if it were a 90° rotation.

This mapping from actual movement to intended movement may be linear or nonlinear. It may be that the user correctly performs very subtle steering motions nearly correctly, and fails on the sharper turns. In this case, the responsiveness of a subtle steering motion may be increased only slightly, or not at all, while the responsiveness of a motion intended to convey sharp steering may be increased more greatly.

In an embodiment, the output is adjusted only after determining that the filter is a filter that may be adjusted. Some filters may benefit from adjustment. For instance, a user who poorly makes a "fire weapon" gesture and frequently misses his intended target may become frustrated with the controls and have a poor user experience. Thus, it may be beneficial to adjust a "fire weapon" filter to aid the user's aim, and the "fire weapon" filter can be a filter that may be adjusted. However, this may not be true for an "automobile steering" gesture. The user may steer very poorly in a conventional sense—he frequently crashes or runs off a track. However some users like to ignore the stated objectives of a scenario and intentionally perform poorly. In such a case, adjusting the "automobile steering" filter may actually damage the user experience because it prevents him from doing what he wants to do. Here, the "automobile steering" gesture may be one that may not be adjusted.

Whether or not a filter may be adjusted may be determined, for instance, by a boolean output by the filter that can be read by an entity that would adjust it, or by a boolean set in a data structure corresponding to the filter that may be read by an entity that would adjust it.

In an embodiment, providing assistance comprises replacing the filter with a second filter. For instance the user may have difficulty performing gestures associated with an "expert steering" filter, which has low tolerances for variances from the exemplary motion. This may be determined and the "expert steering" filter may be replaced with a "beginner steering" filter, which has higher tolerances for variance than the "expert steering filter." The filter may be replaced, for example, by indicating to an associated application that it is to use this new filter's output(s) in place of the former filter's output(s), or by removing the former filter from the gesture recognizer engine and in its place putting the new filter.

In an embodiment, providing assistance comprises suspending an application corresponding to the user-performed gesture. For example, where it is determined that assistance to teach the user how to properly perform the gesture should be given, it would be very difficult for the user to learn the gesture and still interact with the application. So, the application may be paused or suspended, the assistance given for a time, such as until the user has proven to be able to consistently perform the gesture, and after the assistance session, the application may be resumed.

In an embodiment, providing assistance comprises displaying the output to the user on a display device. For instance, where the output comprises the confidence level, the confidence level may be graphed versus time as the user attempts to perform the gesture. When he performs the gesture correctly, he will see the confidence level increase correspondingly, and will be able to associate those movements with correctly performing the gesture. This display may also include an indication of when that output is acceptable, such as via a color change, an alert sound, or a flash on the screen. Where the output is hand distance is graphed versus time, and the hand distance must be between 12" and 18", it may be that the graph is green where the user's hand distance is between 12" and 18", and red at all other times.

In an embodiment, providing assistance comprises displaying a representation of the user-performed gesture and a demonstration of the gesture. This may comprise displaying the two gestures side-by-side so that the user may visually identify where he is moving improperly. Additionally, where the user performs part of the gesture correctly and part of the gesture incorrectly, there may be an indication of those times the user is performing the gesture correctly, such as by playing a sound. Furthermore, the assistance may include a direct instruction regarding the differences between the two gestures, such as on-display text that reads, "Your hands must be 12-18" apart. Your hands appear to be too far apart. Try bringing them closer together."

In an embodiment, providing assistance comprises displaying a difference between the user-performed gesture and the demonstration of the gesture. This may comprise overlaying the demonstration on top of the user-performed gesture so that the differences are apparent. This may include highlighting a region of the body where the difference exists. In an embodiment, the user-performed gesture and the demonstration of the gesture are displayed differently to make them easier to individually identify. For instance, where one is overlaid on the other, the user-performed gesture may be displayed as video of the user or an avatar representation, and the demonstration may be displayed as a wire-frame avatar, or vice versa.

In an embodiment, the assistance is sourced from another user. In an embodiment, the sourced assistance is at least one from a set, the set comprising assistance that is at or near the top of a leader-board, assistance that has been rated highly, assistance that has been identified by a user that created it as being appropriate for assistance, assistance that a second user has identified as being appropriate for the user, assistance from a user of the same culture as the user, assistance from a user of the same language as the user, assistance from a user of a similar age as the user, and assistance from a user of a similar location as the user.

In an embodiment, providing assistance comprises relaxing a tolerance level associated with the filter.

FIGS. 11B and 11C depicts example architectures for gesture coaching 1150 integrated with a gesture recognizer engine 190 and an application 1152.

In FIG. 11B, both the gesture coach 1150 and the application 1152 receive the outputs of each filter 518 from each filter 518. This architecture allows the gesture coach 1150 to monitor filter output to determine whether assistance is appropriate, while at the same time allowing the application 1152 to receive the outputs. Optionally, the gesture coach 1150 may communicate with the application 1152, such as to send modified outputs for use by the application 1152.

In FIG. 11C, the gesture coach 1150 receives the outputs of each filter 518 from those filters 518, and then passes the outputs to the application 1152. In this architecture, the gesture coach 1150 may modify any received output before sending it to the application 1152.

Figure 12A:
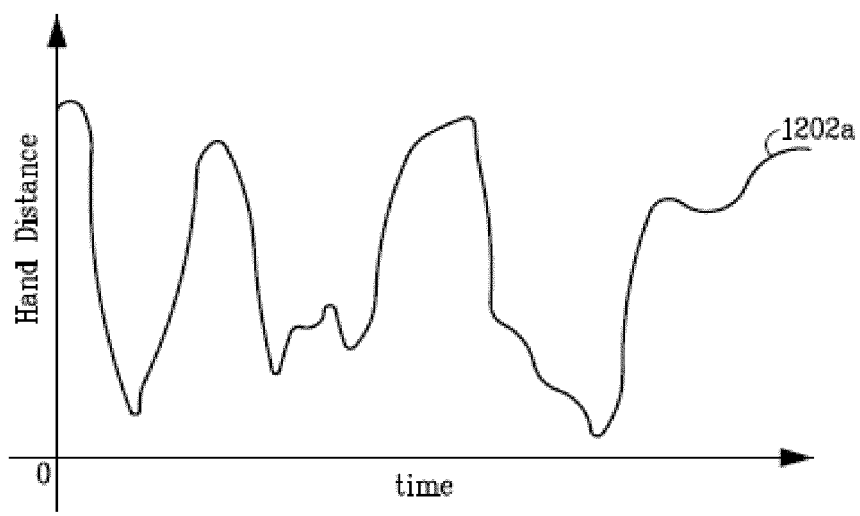
FIGS. 12A and 12B depict example filter outputs from which it may be determined that gesture coaching is appropriate.
Figure 12B:
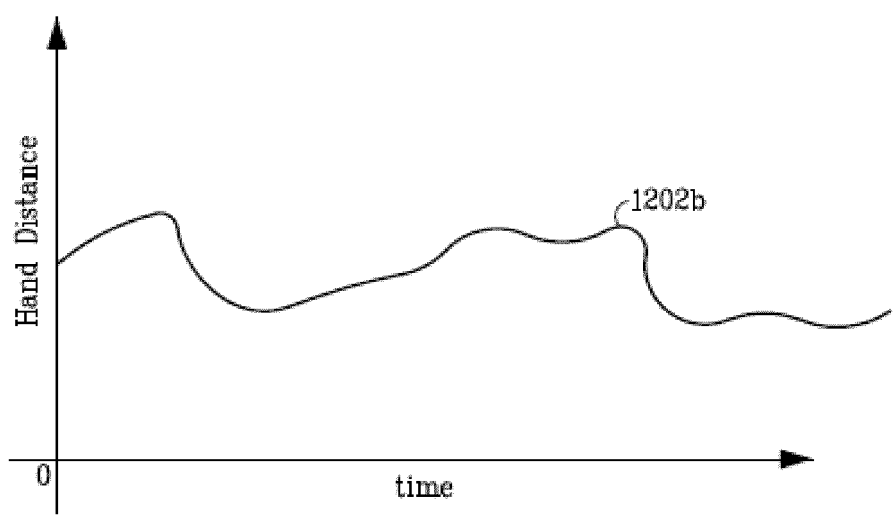

FIGS. 12A and 12B depict example filter outputs from which it may be determined that gesture coaching is appropriate. Each graph charts the user's hand distance over time, as from the output of a "automobile steering" gesture filter.

FIG. 12A depicts exemplary hand distance over time of an unskilled user who has difficulty maintaining a roughly uniform hand distance as is required for the gesture to be performed. It may be determined from such output that assistance is appropriate. Likewise, where the hand distance must lie in a given range, were the user to maintain a roughly uniform hand distance, it may still be determined that assistance is appropriate if that roughly uniform distance is above or below the given range.

FIG. 12B depicts exemplary hand distance over time of an adroit user who is able to maintain a roughly uniform hand distance as is required for the gesture to be performed. While the hand distance is not constant, the filter may allow for such variance so long as it is small enough.

Conclusion

While the present disclosure has been described in connection with the preferred aspects, as illustrated in the various figures, it is understood that other similar aspects may be used or modifications and additions may be made to the described aspects for performing the same function of the present disclosure without deviating therefrom. Therefore, the present disclosure should not be limited to any single aspect, but rather construed in breadth and scope in accordance with the appended claims. For example, the various procedures described herein may be implemented with hardware or software, or a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium. When the program code is loaded into and executed by a machine, such as a computer, the machine becomes an apparatus configured for practicing the disclosed embodiments. In addition to the specific implementations explicitly set forth herein, other aspects and implementations will be apparent to those skilled in the art from consideration of the specification disclosed herein. It is intended that the specification and illustrated implementations be considered as examples only.

What is claimed:

1. A method for providing assistance regarding a user-performed gesture, comprising:
   receiving data captured by a capture device, the data corresponding to a user motion or pose;
   analyzing the data to produce an output corresponding to whether the data corresponds to input recognized by a system;
   determining from the output that it is unlikely that the user correctly performed a user motion or pose that invokes the input recognized by the system;
   determining from the output that the user likely intended to perform the user motion or pose that invokes the input recognized by the system;
   adjusting the output to have a new value, the new value being more indicative of invoking the input recognized by the system than the old value is indicative of invoking the input recognized by the system; and
   sending the adjusted output to an application that is configured to process the input recognized by the system.

2. The method of claim 1, further comprising:
   determining that the output may be adjusted before adjusting the output;
   receiving second data captured by the capture device, the second data corresponding to a second user motion or pose;
   analyzing the second data to produce second output corresponding to whether the second data corresponds to a second input recognized by a system;
   determining from the second output that it is unlikely that the user correctly performed a user motion or pose that invokes the second input recognized by the system;
   determining from the second output that the user likely intended to perform the a user motion or pose that invokes the input recognized by the system;
   providing assistance regarding the a user motion or pose that invokes the input recognized by the system; and
   in response to determining that the second output may not be adjusted, sending the second output to the application without adjusting the second output.

3. The method of claim 1, wherein the output comprises a confidence level that the user correctly performed the user motion or pose that invokes the input recognized by the system.

4. The method of claim 3, wherein it is unlikely that the user correctly performed the system-recognized gesture when the confidence level is below a threshold.

5. The method of claim 1, further comprising:
   suspending an application corresponding to the input recognized by the system in response to determining from the output that it is unlikely that the user correctly performed a user motion or pose that invokes the input recognized by the system.

6. The method of claim 1, wherein the output comprises a value, and further comprising:
   displaying the value of the output to the user on a display device.

7. The method of claim 1, further comprising:
displaying a representation of the user motion or pose corresponding to the data and a demonstration of the user motion or pose that invokes the input recognized by the system.

8. The method of claim 7, further comprising:
displaying a difference between the user motion or pose corresponding to the data and the demonstration of the user motion or pose that invokes the input recognized by the system.

9. A system for providing assistance regarding a user-performed gesture, comprising:
a processor; and
a memory communicatively coupled to the processor when the system is operational, the memory bearing processor-executable instructions that, when executed on the processor, cause the system to at least:
receive data captured by a camera, the data corresponding to a user motion or pose;
analyze the data to produce an output corresponding to whether the data corresponds to input recognized by a system;
determine from the output that it is unlikely that the user correctly performed a user motion or pose that invokes the input recognized by the system;
determine from the output that the user likely intended to perform the user motion or pose that invokes the input recognized by the system;
adjust the output to have a new value, the new value being more indicative of invoking the input recognized by the system than the old value is indicative of invoking the input recognized by the system; and
send the adjusted output to an application that is configured to process the input recognized by the system.

10. The system of claim 9, wherein the output comprises a confidence level the user correctly performed the user motion or pose that invokes the input recognized by the system.

11. The system of claim 10, wherein it is unlikely that the user correctly performed the system-recognized gesture when the confidence level is below a threshold.

12. A computer readable storage medium, comprising computer readable instructions that when executed on a computer, cause the computer to perform operations comprising:
receiving data captured by a depth camera, the data corresponding to a user motion or pose;
analyzing the data to produce an output corresponding to whether the data corresponds to input recognized by a system;
determining from the output that it is unlikely that the user correctly performed a user motion or pose that invokes the input recognized by the system;
determining from the output that the user likely intended to perform the user motion or pose that invokes the input recognized by the system;
adjusting the output to have a new value, the new value being more indicative of invoking the input recognized by the system than the old value is indicative of invoking the input recognized by the system; and
sending the adjusted output to an application that is configured to process the input recognized by the system.

13. The computer readable storage medium of claim 12, further comprising computer readable instructions that when executed on the computer cause the computer to perform operations comprising:
determining that the output may be adjusted before adjusting the output;
receiving second data captured by the capture device, the second data corresponding to a second user motion or pose;
analyzing the second data to produce second output corresponding to whether the second data corresponds to a second input recognized by a system;
determining from the second output that it is unlikely that the user correctly performed a user motion or pose that invokes the second input recognized by the system;
determining from the second output that the user likely intended to perform the a user motion or pose that invokes the input recognized by the system;
providing assistance regarding the a user motion or pose that invokes the input recognized by the system; and
in response to determining that the second output may not be adjusted, sending the second output to the application without adjusting the second output.

14. The computer readable storage medium of claim 12, wherein the output comprises a confidence level that the user correctly performed the user motion or pose that invokes the input recognized by the system.

15. The computer readable storage medium of claim 14, wherein it is unlikely that the user correctly performed the system-recognized gesture when the confidence level is below a threshold.

16. The computer readable storage medium of claim 12, further comprising computer readable instructions that when executed on the computer cause the computer to perform operations comprising:
suspending an application corresponding to the input recognized by the system in response to determining from the output that it is unlikely that the user correctly performed a user motion or pose that invokes the input recognized by the system.

17. The computer readable storage medium of claim 12, wherein the output comprises a value, and further comprising:
displaying the value of the output to the user on a display device.

18. The computer readable storage medium of claim 12, further comprising computer readable instructions that when executed on the computer cause the computer to perform operations comprising:
displaying a representation of the user motion or pose corresponding to the data and a demonstration of the user motion or pose that invokes the input recognized by the system.

19. The computer readable storage medium of claim 18, further comprising computer readable instructions that when executed on the computer cause the computer to perform operations comprising:
displaying a difference between the user motion or pose corresponding to the data and the demonstration of the user motion or pose that invokes the input recognized by the system.

* * * * *